(12) United States Patent  (10) Patent No.: US 7,670,334 B2
Hueil et al.  (45) Date of Patent: Mar. 2, 2010

(54) SURGICAL INSTRUMENT HAVING AN ARTICULATING END EFFECTOR

(75) Inventors: Geoffrey C. Hueil, Mason, OH (US); Joseph Charles Hueil, Loveland, OH (US); Kenneth Edward Hogue, Mason, OH (US); Douglas Jon Siebenaler, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 902 days.

(21) Appl. No.: 11/329,020

(22) Filed: Jan. 10, 2006

(65) Prior Publication Data

US 2007/0158385 A1  Jul. 12, 2007

(51) Int. Cl.
  *A61B 17/00* (2006.01)
(52) U.S. Cl. ............... 606/1; 227/175.1; 606/139; 606/205
(58) Field of Classification Search ............ 606/51, 606/52, 205, 1, 139–142; 600/104, 141, 600/142; 227/175.1, 176.1
See application file for complete search history.

(56) References Cited

U.S. PATENT DOCUMENTS

| 2,037,727 | A | 4/1936 | Chapelle |
| 3,269,630 | A | 8/1966 | Fleischer |
| 3,734,207 | A | 5/1973 | Fishbein |
| 3,892,228 | A | 7/1975 | Mitsui |
| 3,894,174 | A | 7/1975 | Cartun |
| 3,940,844 | A | 3/1976 | Colby et al. |
| 4,415,112 | A | 11/1983 | Green |
| 4,475,679 | A | 10/1984 | Fleury, Jr. |
| 4,520,817 | A | 6/1985 | Green |
| 4,526,174 | A | 7/1985 | Froehlich |

(Continued)

FOREIGN PATENT DOCUMENTS

CA  2458946 A1  3/2003

(Continued)

OTHER PUBLICATIONS

European Search Report, Application No. 07250077.0, dated May 3, 2007 (7 pages).

(Continued)

*Primary Examiner*—Todd E Manahan
*Assistant Examiner*—Jennifer L Hornberger
(74) *Attorney, Agent, or Firm*—Dean Garner

(57) ABSTRACT

An articulating surgical instrument is shown, which comprises a shaft and an end effector. The shaft has a longitudinal axis, and the end effector is operationally coupled, preferably mechanically coupled, to the shaft at an articulation pivot. The instrument also comprises a first band, and in some embodiments, a second band, each operationally connected to the end effector and extending through at least a portion of the shaft. An articulation control applies a force in a direction substantially transverse to the longitudinal axis, wherein the force, when applied in one direction, is translated through the first band to the end effector to effect rotation of the end effector relative to the shaft about the articulation pivot in a first rotational direction, and when the force is applied in the opposite direction, is translated through the second band to the end effector to effect rotation of the end effector relative to the shaft about the articulation pivot in a second rotational direction.

26 Claims, 19 Drawing Sheets

U.S. PATENT DOCUMENTS

| | | | |
|---|---|---|---|
| 4,605,001 A | 8/1986 | Rothfuss et al. | |
| 4,606,343 A | 8/1986 | Conta et al. | |
| 4,608,981 A | 9/1986 | Rothfuss et al. | |
| 4,709,120 A | 11/1987 | Pearson | |
| 4,715,520 A | 12/1987 | Roehr, Jr. et al. | |
| 4,728,876 A | 3/1988 | Mongeon et al. | |
| 4,869,415 A | 9/1989 | Fox | |
| 4,880,015 A | 11/1989 | Nierman | |
| 4,892,244 A | 1/1990 | Fox et al. | |
| 4,941,623 A | 7/1990 | Pruitt | |
| 4,955,959 A | 9/1990 | Tompkins et al. | |
| 4,978,049 A | 12/1990 | Green | |
| 5,027,834 A | 7/1991 | Pruitt | |
| 5,031,814 A | 7/1991 | Tompkins et al. | |
| 5,040,715 A | 8/1991 | Green et al. | |
| 5,065,929 A | 11/1991 | Schulze et al. | |
| 5,080,556 A | 1/1992 | Carreno | |
| 5,104,025 A | 4/1992 | Main et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,156,315 A | 10/1992 | Green et al. | |
| 5,200,280 A | 4/1993 | Karasa | |
| 5,207,697 A | 5/1993 | Carusillo et al. | |
| 5,211,649 A | 5/1993 | Kohler et al. | |
| 5,246,156 A | 9/1993 | Rothfuss et al. | |
| 5,253,793 A | 10/1993 | Green et al. | |
| RE34,519 E | 1/1994 | Fox et al. | |
| 5,275,323 A | 1/1994 | Schulze et al. | |
| 5,307,976 A | 5/1994 | Olson et al. | |
| 5,309,927 A | 5/1994 | Welch | |
| 5,318,221 A | 6/1994 | Green et al. | |
| 5,330,502 A | 7/1994 | Hassler et al. | |
| 5,332,142 A | 7/1994 | Robinson et al. | |
| 5,339,799 A | 8/1994 | Kami et al. | |
| 5,350,400 A | 9/1994 | Esposito et al. | |
| 5,379,933 A | 1/1995 | Green et al. | |
| 5,383,880 A | 1/1995 | Hooven | |
| 5,389,098 A | 2/1995 | Tsuruta et al. | |
| 5,391,180 A | 2/1995 | Tovey et al. | |
| 5,395,033 A | 3/1995 | Byrne et al. | |
| 5,395,312 A | 3/1995 | Desai | |
| 5,397,046 A | 3/1995 | Savage et al. | |
| 5,403,312 A | 4/1995 | Yates et al. | |
| 5,405,344 A * | 4/1995 | Williamson et al. | 606/1 |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,433,721 A | 7/1995 | Hooven et al. | |
| 5,445,304 A | 8/1995 | Plyley et al. | |
| 5,456,401 A | 10/1995 | Green et al. | |
| 5,462,215 A | 10/1995 | Viola et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,476,479 A | 12/1995 | Green et al. | |
| 5,478,003 A | 12/1995 | Green et al. | |
| 5,480,409 A | 1/1996 | Riza | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,503,320 A | 4/1996 | Webster et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,549,628 A | 8/1996 | Cooper et al. | |
| 5,553,675 A | 9/1996 | Pitzen et al. | |
| 5,554,169 A | 9/1996 | Green et al. | |
| 5,562,239 A | 10/1996 | Boiarski et al. | |
| 5,562,241 A | 10/1996 | Knodel et al. | |
| 5,574,431 A | 11/1996 | McKeown et al. | |
| 5,575,803 A | 11/1996 | Cooper et al. | |
| 5,582,611 A | 12/1996 | Tsuruta et al. | |
| 5,584,425 A | 12/1996 | Savage et al. | |
| 5,586,711 A | 12/1996 | Plyley et al. | |
| 5,618,303 A | 4/1997 | Marlow et al. | |
| 5,628,446 A | 5/1997 | Geiste et al. | |
| 5,632,432 A | 5/1997 | Schulze et al. | |
| 5,636,779 A | 6/1997 | Palmer | |
| 5,651,491 A | 7/1997 | Heaton et al. | |
| 5,653,374 A | 8/1997 | Young et al. | |
| 5,662,258 A | 9/1997 | Knodel et al. | |
| 5,667,517 A | 9/1997 | Hooven | |
| 5,673,840 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,688,270 A | 11/1997 | Yates et al. | |
| 5,692,668 A | 12/1997 | Schulze et al. | |
| 5,693,042 A | 12/1997 | Boiarski et al. | |
| 5,702,408 A | 12/1997 | Wales et al. | |
| 5,704,534 A | 1/1998 | Huitema et al. | |
| 5,706,998 A | 1/1998 | Plyley et al. | |
| 5,709,680 A | 1/1998 | Yates et al. | |
| 5,713,505 A | 2/1998 | Huitema | |
| 5,715,988 A | 2/1998 | Palmer | |
| 5,718,359 A | 2/1998 | Palmer et al. | |
| 5,735,445 A | 4/1998 | Vidal et al. | |
| 5,747,953 A | 5/1998 | Philipp | |
| 5,749,893 A | 5/1998 | Vidal et al. | |
| 5,752,644 A | 5/1998 | Bolanos et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,782,397 A | 7/1998 | Koukline | |
| 5,782,859 A | 7/1998 | Nicholas et al. | |
| 5,796,188 A | 8/1998 | Bays | |
| 5,797,537 A | 8/1998 | Oberlin et al. | |
| 5,797,538 A | 8/1998 | Heaton et al. | |
| 5,807,393 A | 9/1998 | Williamson, IV et al. | |
| 5,817,093 A | 10/1998 | Williamson, IV et al. | |
| 5,823,066 A | 10/1998 | Huitema et al. | |
| 5,826,776 A | 10/1998 | Schulze et al. | |
| 5,833,690 A | 11/1998 | Yates et al. | |
| 5,839,639 A | 11/1998 | Sauer et al. | |
| 5,843,132 A | 12/1998 | Ilvento | |
| 5,865,361 A | 2/1999 | Milliman et al. | |
| 5,871,135 A | 2/1999 | Williamson, IV et al. | |
| 5,878,938 A | 3/1999 | Bittner et al. | |
| 5,893,506 A | 4/1999 | Powell | |
| 5,894,979 A | 4/1999 | Powell | |
| 5,911,353 A | 6/1999 | Bolanos et al. | |
| 5,918,791 A | 7/1999 | Sorrentino et al. | |
| 5,951,552 A | 9/1999 | Long et al. | |
| 5,954,259 A | 9/1999 | Viola et al. | |
| 5,988,479 A | 11/1999 | Palmer | |
| 6,010,054 A | 1/2000 | Johnson et al. | |
| 6,017,356 A | 1/2000 | Frederick et al. | |

| Patent/Publication | Date | Name |
|---|---|---|
| 6,022,352 A | 2/2000 | Vandewalle |
| 6,024,741 A | 2/2000 | Williamson, IV et al. |
| 6,024,748 A | 2/2000 | Manzo et al. |
| 6,032,849 A | 3/2000 | Mastri et al. |
| 6,079,606 A | 6/2000 | Milliman et al. |
| 6,083,234 A | 7/2000 | Nicholas et al. |
| 6,109,500 A | 8/2000 | Alli et al. |
| H1904 H | 10/2000 | Yates et al. |
| 6,126,670 A | 10/2000 | Walker et al. |
| 6,131,789 A | 10/2000 | Schulze et al. |
| 6,155,473 A | 12/2000 | Tompkins et al. |
| 6,156,056 A | 12/2000 | Kearns et al. |
| 6,202,914 B1 | 3/2001 | Geiste et al. |
| 6,223,835 B1 | 5/2001 | Habedank et al. |
| 6,241,139 B1 | 6/2001 | Milliman et al. |
| 6,250,532 B1 | 6/2001 | Green et al. |
| 6,264,087 B1 | 7/2001 | Whitman |
| 6,273,897 B1 | 8/2001 | Dalessandro et al. |
| 6,309,403 B1 | 10/2001 | Minor et al. |
| 6,315,184 B1 | 11/2001 | Whitman |
| 6,320,123 B1 | 11/2001 | Reimers |
| 6,325,810 B1 | 12/2001 | Hamilton et al. |
| 6,330,965 B1 | 12/2001 | Milliman et al. |
| 6,358,224 B1 | 3/2002 | Tims et al. |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,503,257 B2 | 1/2003 | Grant et al. |
| 6,511,468 B1 | 1/2003 | Cragg et al. |
| 6,522,101 B2 | 2/2003 | Malackowski |
| 6,592,597 B2 | 7/2003 | Grant et al. |
| 6,602,252 B2 | 8/2003 | Mollenauer |
| 6,619,529 B2 | 9/2003 | Green et al. |
| 6,620,166 B1 | 9/2003 | Wenstrom, Jr. et al. |
| 6,629,988 B2 | 10/2003 | Weadock |
| RE38,335 E * | 11/2003 | Aust et al. ............... 606/170 |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,716,232 B1 | 4/2004 | Vidal et al. |
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,814,741 B2 | 11/2004 | Bowman et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,828,902 B2 | 12/2004 | Casden |
| 6,830,174 B2 | 12/2004 | Hillstead et al. |
| 6,835,199 B2 | 12/2004 | McGuckin, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,818 B2 | 2/2006 | Shelton, IV et al. |
| 7,032,798 B2 | 4/2006 | Whitman et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,066,944 B2 | 6/2006 | Laufer et al. |
| 7,077,856 B2 | 7/2006 | Whitman |
| 7,083,075 B2 | 8/2006 | Swayze et al. |
| 7,090,684 B2 | 8/2006 | McGuckin, Jr. et al. |
| 7,098,794 B2 | 8/2006 | Lindsay et al. |
| 7,140,527 B2 | 11/2006 | Ehrenfels et al. |
| 7,300,450 B2 | 11/2007 | Vleugels et al. |
| 7,416,101 B2 | 8/2008 | Shelton, IV et al. |
| 7,438,209 B1 | 10/2008 | Hess et al. |
| 7,441,685 B1 | 10/2008 | Boudreaux |
| 7,490,749 B2 | 2/2009 | Schall et al. |
| 7,510,107 B2 | 3/2009 | Timm et al. |
| 2002/0165541 A1 | 11/2002 | Whitman |
| 2003/0105478 A1 | 6/2003 | Whitman et al. |
| 2003/0130677 A1 | 7/2003 | Whitman et al. |
| 2003/0216778 A1 | 11/2003 | Weadock |
| 2004/0028502 A1 | 2/2004 | Cummins |
| 2004/0034348 A1 * | 2/2004 | Rashidi ..................... 606/41 |
| 2004/0094597 A1 | 5/2004 | Whitman et al. |
| 2004/0097987 A1 | 5/2004 | Pugsley et al. |
| 2004/0111081 A1 | 6/2004 | Whitman et al. |
| 2004/0122471 A1 | 6/2004 | Toby et al. |
| 2004/0167572 A1 | 8/2004 | Roth et al. |
| 2004/0222268 A1 | 11/2004 | Bilotti et al. |
| 2004/0232199 A1 | 11/2004 | Shelton, IV et al. |
| 2004/0243151 A1 | 12/2004 | Demmy et al. |
| 2004/0243176 A1 | 12/2004 | Hahnen et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0033357 A1 | 2/2005 | Braun |
| 2005/0070958 A1 | 3/2005 | Swayze et al. |
| 2005/0072827 A1 | 4/2005 | Mollenauer |
| 2005/0107824 A1 | 5/2005 | Hillstead et al. |
| 2005/0119669 A1 | 6/2005 | Demmy |
| 2005/0131390 A1 | 6/2005 | Heinrich et al. |
| 2005/0143759 A1 | 6/2005 | Kelly |
| 2005/0165415 A1 | 7/2005 | Wales |
| 2005/0173490 A1 | 8/2005 | Shelton, IV |
| 2005/0187576 A1 | 8/2005 | Whitman et al. |
| 2005/0189397 A1 | 9/2005 | Jankowski |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0263562 A1 | 12/2005 | Shelton, IV et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton |
| 2006/0047303 A1 | 3/2006 | Ortiz et al. |
| 2006/0047308 A1 | 3/2006 | Ortiz et al. |
| 2006/0087442 A1 | 4/2006 | Smith et al. |
| 2006/0100643 A1 | 5/2006 | Laufer et al. |
| 2006/0122636 A1 | 6/2006 | Bailley et al. |
| 2006/0142772 A1 | 6/2006 | Ralph et al. |
| 2006/0151567 A1 | 7/2006 | Roy |
| 2006/0190028 A1 | 8/2006 | Wales et al. |
| 2006/0190029 A1 | 8/2006 | Wales |
| 2006/0190031 A1 | 8/2006 | Wales et al. |
| 2006/0212069 A1 | 9/2006 | Shelton, IV |
| 2006/0229665 A1 | 10/2006 | Wales et al. |
| 2006/0278680 A1 | 12/2006 | Viola et al. |
| 2006/0278681 A1 | 12/2006 | Viola et al. |
| 2007/0027469 A1 | 2/2007 | Smith et al. |
| 2007/0034668 A1 | 2/2007 | Holsten et al. |
| 2007/0045379 A1 | 3/2007 | Shelton |
| 2007/1007334 | 3/2007 | Shelton, IV et al. |
| 2007/0075114 A1 | 4/2007 | Shelton, IV et al. |

| Publication No. | Date | Inventor |
|---|---|---|
| 2007/0083234 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0152014 A1 | 7/2007 | Gillum et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0033548 B1 | 5/1986 |
| EP | 0276104 A2 | 7/1988 |
| EP | 0639349 A2 | 2/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0669104 A1 | 8/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |

| | | | |
|---|---|---|---|
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1621138 A2 | 2/2006 |
| EP | 1621141 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1300117 B1 | 8/2007 |
| EP | 1813199 A1 | 8/2007 |
| EP | 1813207 A1 | 8/2007 |
| EP | 1839596 A2 | 2/2008 |
| EP | 1897502 A1 | 3/2008 |
| FR | 999646 A | 2/1952 |
| FR | 1112936 A | 3/1956 |
| FR | 2765794 A | 1/1999 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/35464 A1 | 11/1996 |
| WO | WO 97/34533 A1 | 9/1997 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A2 | 8/2006 |
| WO | WO 2006/132992 A1 | 12/2006 |
| WO | WO 2007/016290 A2 | 2/2007 |
| WO | WO 2007/121579 A1 | 11/2007 |
| WO | WO 2007/142625 A2 | 12/2007 |
| WO | WO 2008/045383 A2 | 4/2008 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

* cited by examiner

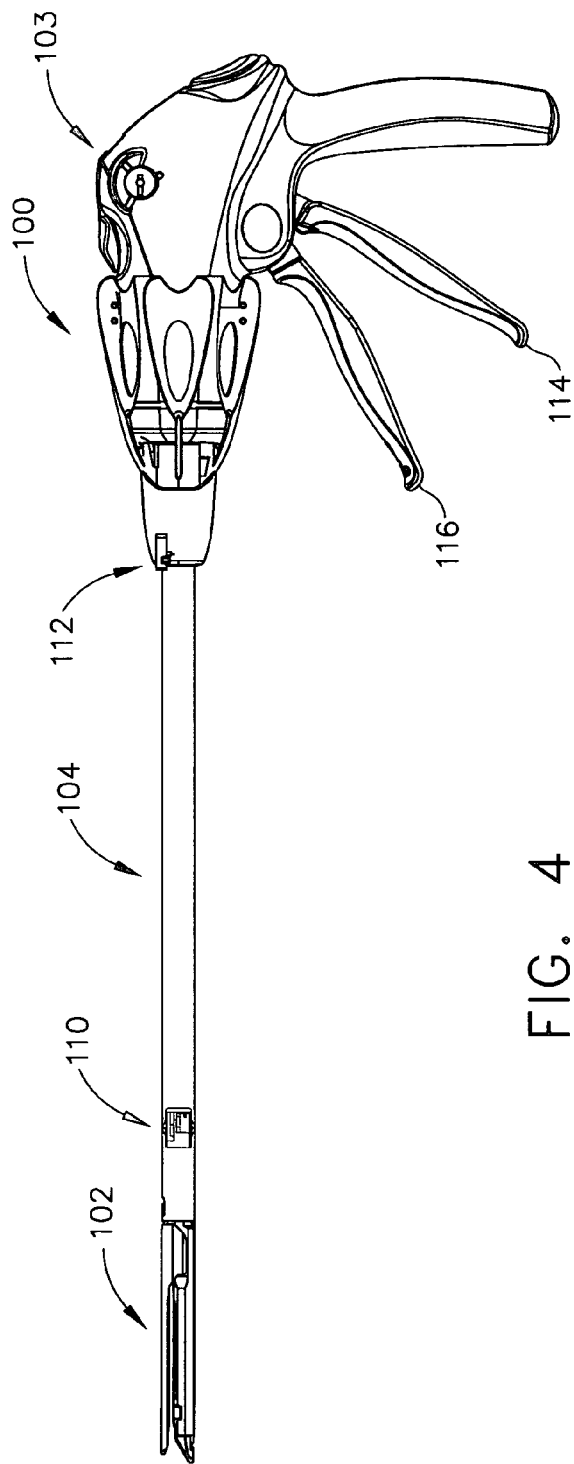
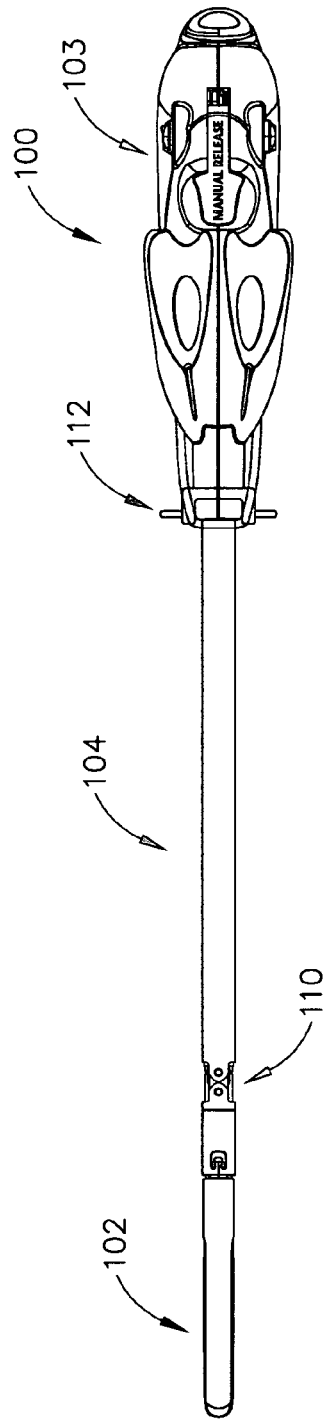
FIG. 4
FIG. 5

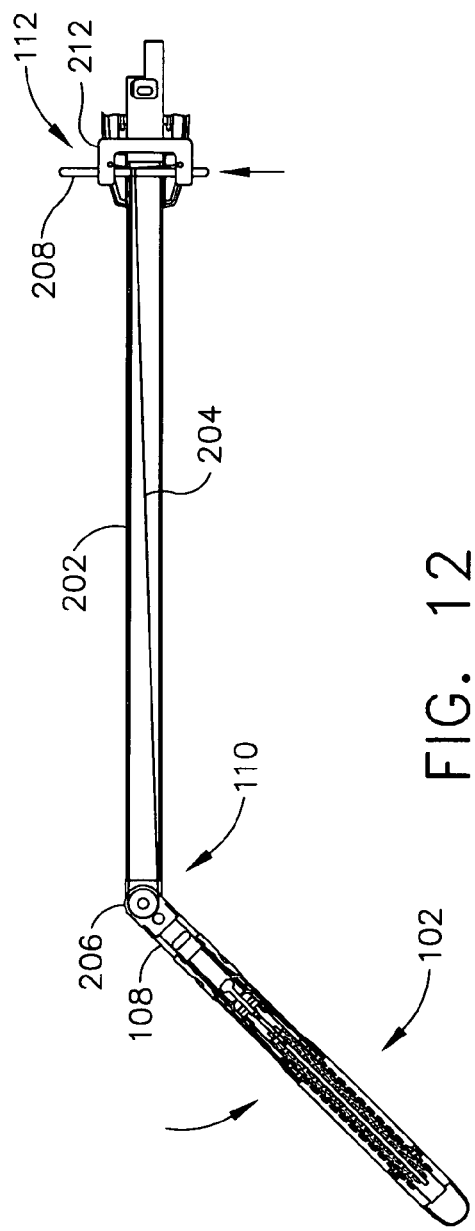
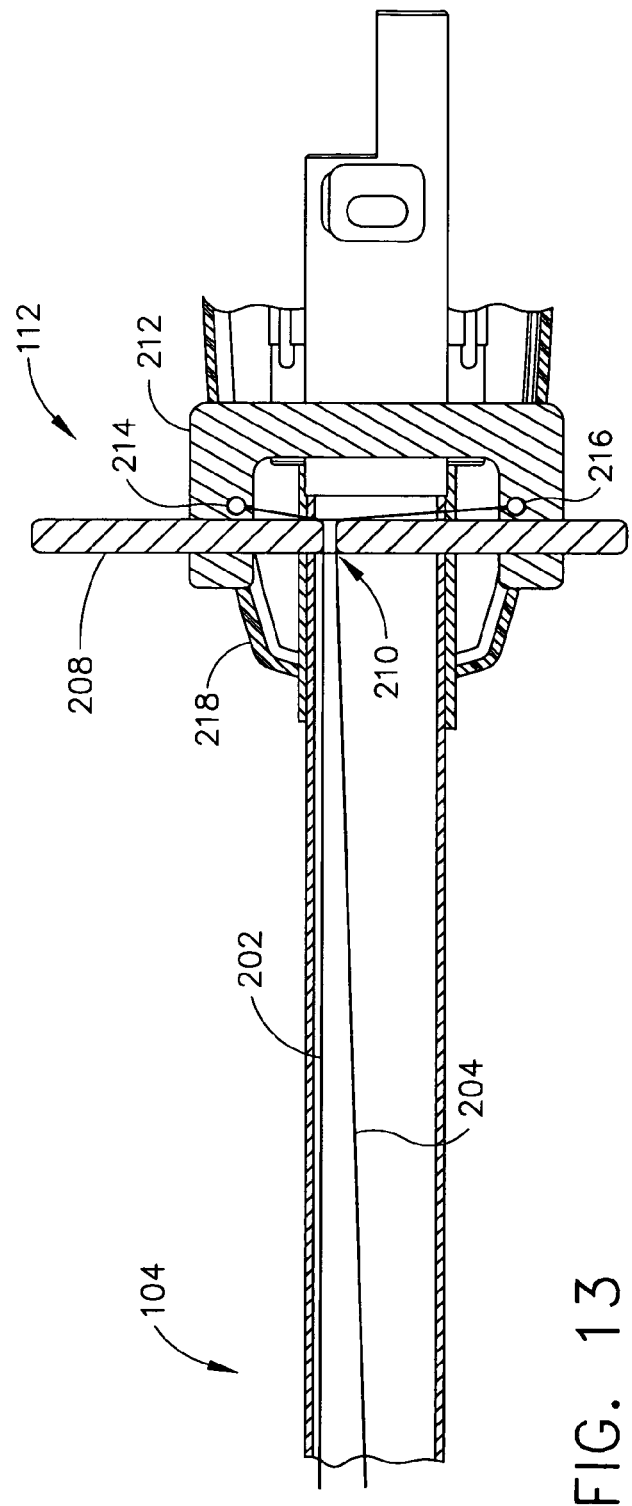
FIG. 12
FIG. 13

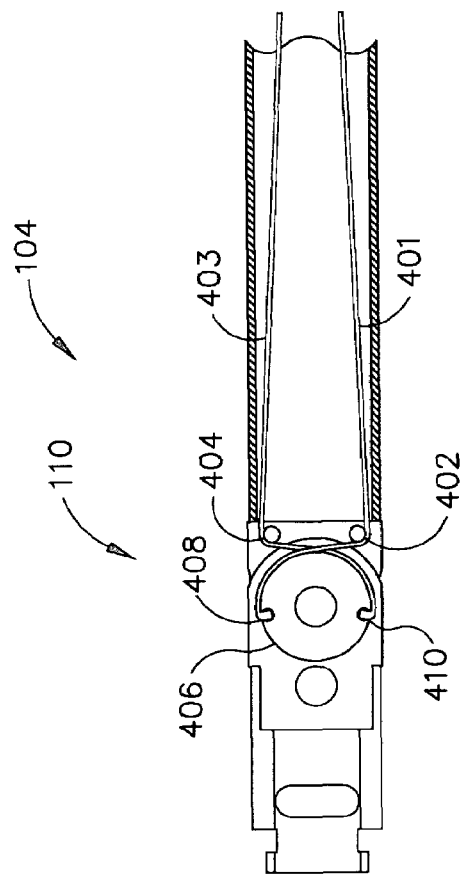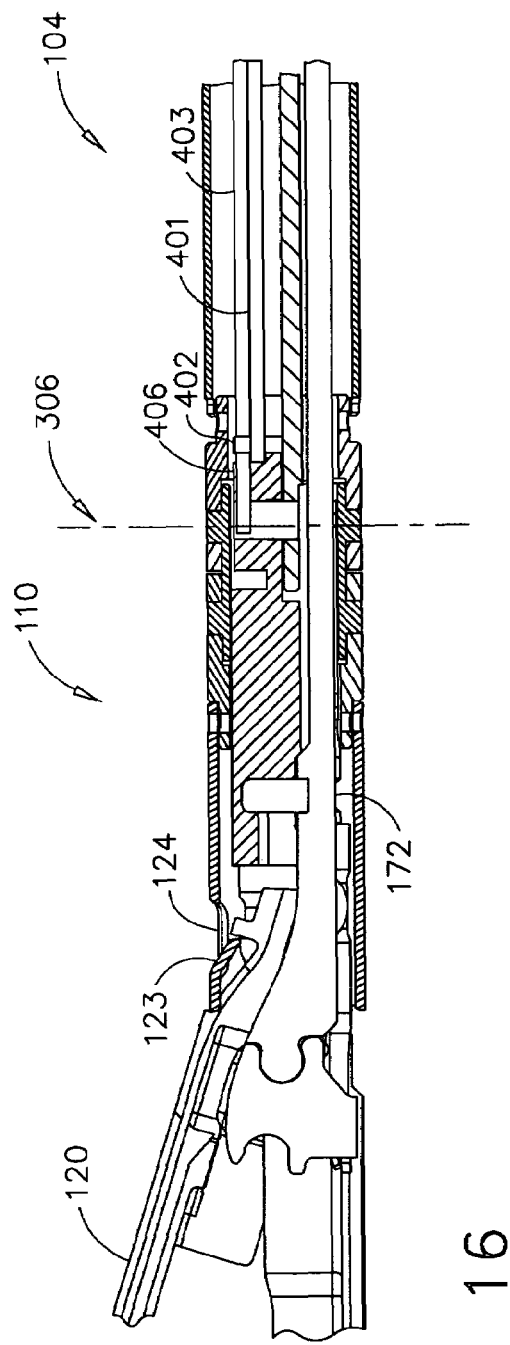
FIG. 14
FIG. 16

SURGICAL INSTRUMENT HAVING AN ARTICULATING END EFFECTOR

FIELD OF THE INVENTION

The present invention relates in general to surgical instruments, and more particularly to minimally invasive surgical instruments having an articulating end effector.

BACKGROUND OF THE INVENTION

Endoscopic and other minimally invasive surgical instruments typically include an end effector positioned at the distal end of an elongate shaft and a handle at the proximal end of the elongate shaft allowing a clinician to manipulate the end effector. In use, the end effector is provided to a surgical site through a cannula of a trocar. At the surgical site, the end effector engages tissue in any number of ways to achieve a diagnostic or therapeutic effect. Endoscopic surgical instruments are often preferred over traditional open surgical instruments because they require smaller incisions that generally heal with less post-operative recovery time than traditional open surgery incisions. Because of this and other benefits of endoscopic surgery, significant development has gone into a range of endoscopic surgical instruments having end effectors that engage tissue to accomplish a number of surgical tasks. For example, end effectors have been developed to act as endocutters, graspers, cutters, staplers, clip appliers, access devices, drug/gene therapy delivery devices, ultrasound, RF, or laser energy devices, and other surgical instruments.

FIGS. 1 & 2 show an exemplary prior art surgical and stapling instrument 10 including an end effector 12 configured as an endocutter for clamping, severing and stapling tissue, for example, as disclosed in U.S. Application Publication No. 2004/0232196 A1, the disclosure of which is herein incorporated by reference in its entirety. The surgical stapling and severing instrument 10 includes a handle portion 20 connected to an implement portion 22, the latter further comprising a shaft 23 distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

Closure trigger 26 is actuated first. Once the clinician is satisfied with the positioning of the end effector 12, the clinician may draw back the closure trigger 26 to its fully closed, locked position proximate to the pistol grip 24. Then, the firing trigger 28 is actuated. The firing trigger 28 springedly returns when the clinician removes pressure. A release button 30 when depressed on the proximal end of the handle portion 20 releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 opens, pivoting away from the elongate channel 16 and translating proximally with the closure sleeve 32. The elongate channel 16 receives a staple cartridge 37.

With particular reference to FIG. 2, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38.

Firing bar 14 also includes a lower most pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped therebetween.

The firing bar 14 advantageously includes a middle pin 46 that passes through a firing drive slot 47 formed in a lower surface of the cartridge 37 and an upward surface of the elongate channel 16, thereby driving the staples therein as described below. The middle pin 46, by sliding against the lower surface of the cartridge 37, advantageously resists any tendency for the end effector 12 to be pinched shut at its distal end.

A distally presented cutting edge 48 between the upper and middle pins 38, 46 on the firing bar 14 traverses through the cartridge 37 to sever clamped tissue. The affirmative positioning of the firing bar 14 with regard to the elongate channel 16 and anvil 18 assure that an effective cut is performed.

The affirmative vertical spacing provided by the E-Beam firing bar 14 is suitable for the limited size available for endoscopic devices. Moreover, the E-Beam firing bar 14 enables fabrication of an anvil 18 with a camber imparting a vertical deflection at its distal end. This cambered anvil 18 advantageously assists in achieving the desired gap in the end effector 12 even with an anvil 18 of reduced thickness, which is thus more suited to the size limitations of an endoscopic device.

The E-Beam firing bar 14 further enables increased applications, especially in combination with a range of configurations of staple cartridges. For instance, a clinician may select a gray staple cartridge yielding a 0.02 mm tissue gap, a white staple cartridge yielding a 0.04 mm tissue gap, a blue cartridge yielding a 0.06 mm tissue gap, or a green cartridge yielding a 0.10 mm tissue gap. The vertical height of each respective staple cartridge in combination with the length of staples and an integral wedge sled 50 predetermines this desired tissue thickness with the anvil 18 appropriately vertically spaced by the E-Beam firing bar 14.

With surgical instrument 10 as well as other minimally invasive instruments, the positioning of the end effector at the surgical site is constrained by the trocar. Generally the elongate shaft 23 enables the clinician to insert the end effector to a desired depth and rotate the end effector about the longitudinal axis of the shaft. This allows the end effector to be positioned at the surgical site, to a degree. With judicious placement of the trocar and use of graspers, for instance, through another trocar, this amount of positioning is often sufficient. Depending upon the nature of the operation, however, it may be desirable to adjust the positioning of the end effector of an endoscopic surgical instrument. In particular, it is often desirable to orient the end effector at any one of multiple angles relative to the longitudinal axis of the elongate shaft of the instrument.

Movement of the end effector through multiple angles relative to the instrument shaft is conventionally referred to as "articulation." Articulation is typically accomplished by a pivot (or articulation) joint being placed in the elongate shaft just proximal to the end effector. This allows the clinician to articulate the end effector remotely to either side for better surgical placement of the staple lines and easier tissue manipulation and orientation. An articulating end effector permits the clinician to more easily engage tissue in some instances, such as behind an organ. In addition, articulated positioning advantageously allows an endoscope to be positioned behind the end effector without being blocked by the elongate shaft.

Approaches to articulating end effectors tend to be complicated because mechanisms for controlling the articulation must be integrated with mechanisms for operating the end effector. For example the closure sleeve, drive member and mechanisms for articulation must be implemented within the small diameter constraints of the instrument's shaft. One common design involves an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

While this generally-known approach successfully articulates the end effector about an articulation pivot, it is desirable to further enhance performance. Consequently, a significant need exists for an improved articulating surgical instrument.

BRIEF SUMMARY OF THE INVENTION

In accordance with one embodiment of the invention, there is provided an articulating surgical instrument. The instrument in this embodiment comprises a shaft and an end effector. The shaft has a longitudinal axis, and the end effector is operationally coupled, preferably mechanically coupled, to the shaft at an articulation pivot. The instrument also comprises a first band operationally connected to the end effector and extending through at least a portion of the shaft. An articulation control applies a force in a direction substantially transverse to the longitudinal axis. The articulation control is operationally connected to the first band such that application of the force is translated through the first band to the end effector to effect rotation of the end effector relative to the shaft about the articulation pivot.

In accordance with another embodiment having a shaft and end effector as described above, a second band is operationally connected to and extends from the end effector through at least a portion of the shaft. In this embodiment, the articulation control is also configured to apply the force in a second direction substantially transverse to the longitudinal axis. The force is translated through the second band to the end effector to effect rotation of the end effector relative to the shaft about the articulation pivot in a second rotational direction.

The articulation control in one embodiment may be structured for movement in a first direction for applying the force in a first transverse direction to effect rotation of the end effector in a first rotational direction relative to the shaft. In this embodiment, the articulation control may also be structured for movement in a second direction for applying the force in a second transverse direction, opposite to the first transverse direction, to effect rotation of the end effector in a second rotational direction relative to the shaft.

The articulation control may include an articulation slide that is movable transversely across the shaft to first, second and neutral positions. The articulation slide defines a slot positioned at about the longitudinal axis when the articulation slide is in the neutral position and the first and second bands pass through the slot. The articulation slot is offset from the longitudinal axis when the articulation slide is in either one of the first or the second positions.

In various embodiments, the first band and the second band are pre-bent toward the longitudinal axis when the articulation control is in a neutral position, when no force is applied to the articulation control. In yet another embodiment having a shaft and end effector, the first band has a first end mechanically coupled to the end effector at a point offset from the articulation axis.

In accordance with another embodiment having a shaft and end effector as described above, the instrument has a first hydraulic articulation bladder expandable toward the first band. A hydraulic actuation bladder is fluidically coupled to the first hydraulic articulation bladder. Also, in various embodiments, a first actuation button is positioned to compress the first hydraulic actuation bladder. Compression of the first hydraulic actuation bladder causes the first hydraulic articulation bladder to inflate. Expansion of the first hydraulic articulation bladder toward the first band causes bending of the first band which effects rotation of the end effector relative to the shaft about the articulation pivot in a first rotational direction. In another embodiment of the instrument, a second hydraulic articulation bladder may be provided. Expansion of the second hydraulic articulation bladder toward the second band causes bending of the second band which effects rotation of the end effector relative to the shaft about the articulation pivot in a second rotational direction.

In accordance with another embodiment of the invention, there is provided a method for operating the instrument. The method may comprise the step of applying a force to the instrument in a direction that is substantially transverse to the shaft, wherein the force causes the first band to bend, and wherein the bending of the first band causes the end effector to pivot relative to the shaft about the articulation pivot in a first direction.

BRIEF DESCRIPTION OF THE FIGURES

The accompanying drawings, which are incorporated in and constitute part of the specification, illustrate embodiments of the invention and, together with the general description of the invention given above, and the detailed description of the embodiments given below, serve to explain the principles of the present invention.

FIG. 4 depicts side view of a surgical instrument according to various embodiments of the present invention;

FIG. 5 depicts a top down view of a surgical instrument according to various embodiments of the present invention;

FIG. 12 depicts an end effector, articulation pivot, and articulation control of the surgical instrument of FIG. 6 with the end effector articulated to the left according to various embodiments of the present invention;

FIG. 13 depicts a top down cross-section view of an articulation control of the surgical instrument of FIG. 6 pushed to the left to move the end effector as shown in FIG. 12;

FIG. 14 depicts a top down cross-section view of an articulation pivot of a surgical instrument according to another embodiment of the present invention;

FIG. 16 depicts a side cross-section view of another embodiment of the articulation pivot of a surgical instrument having the articulation pivot of FIG. 14;

DETAILED DESCRIPTION OF THE INVENTION

Figure 1:
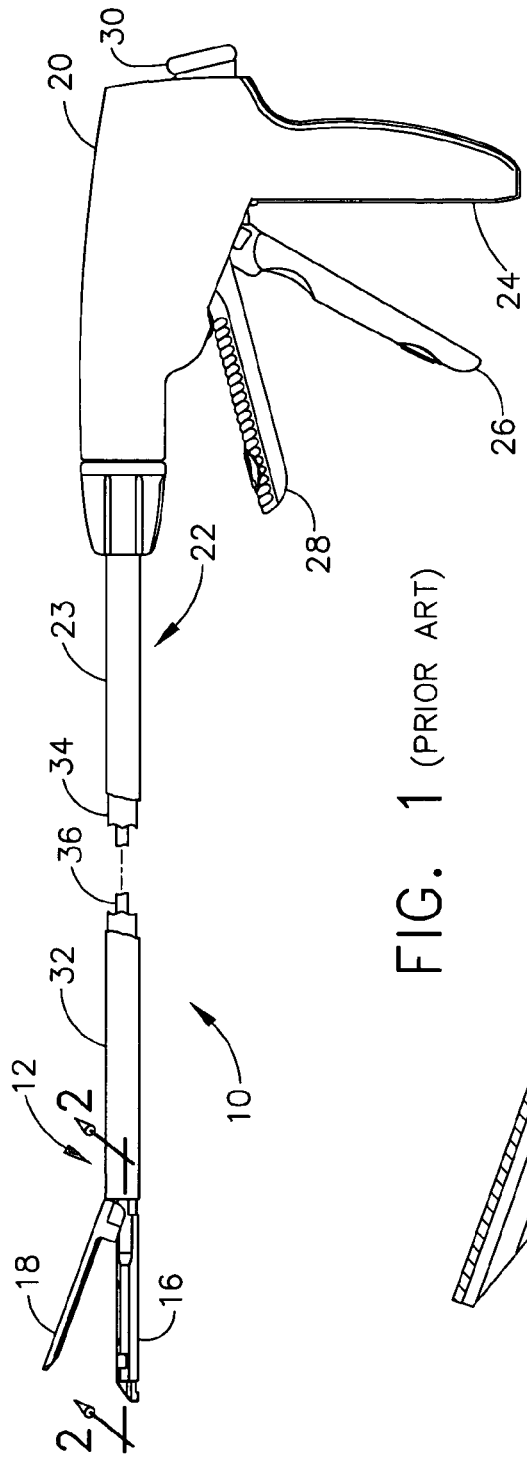
FIG. 1 depicts a partially cut-away side elevation view of a prior art surgical instrument.
Figure 2:
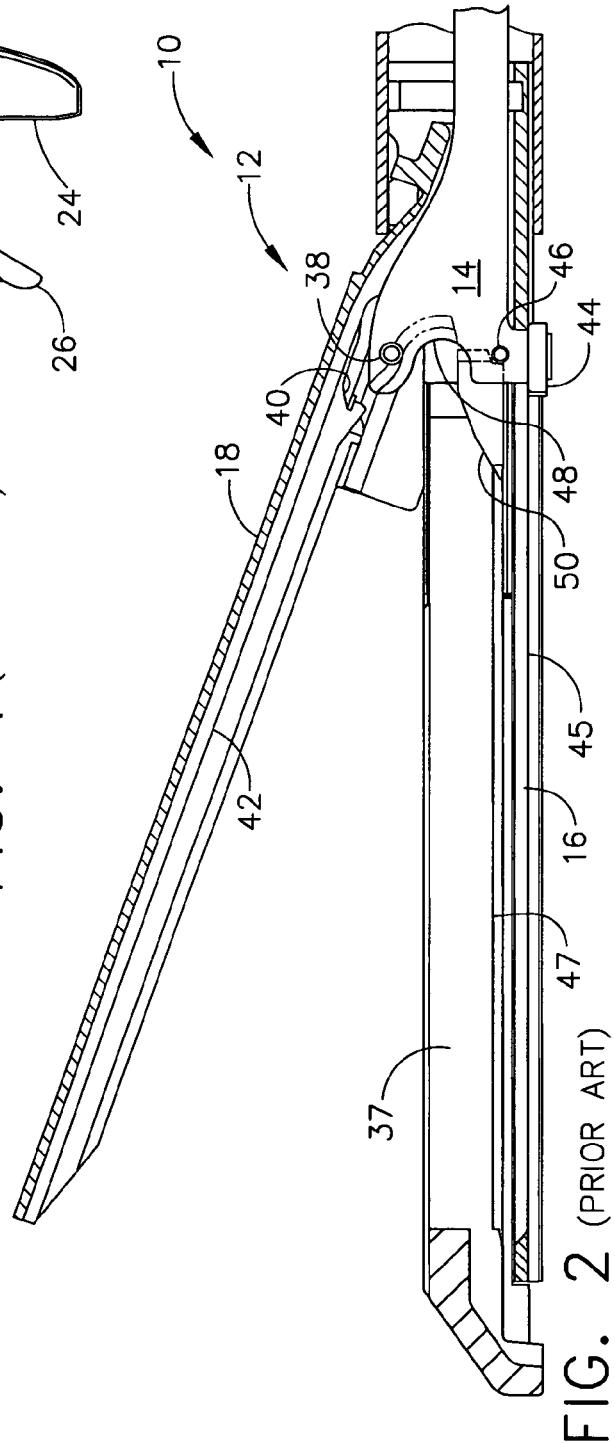
FIG. 2 depicts a cross-sectional side elevation detail view along the line 2-2 of FIG. 1 of an end effector of the prior art surgical instrument.
Figure 3:
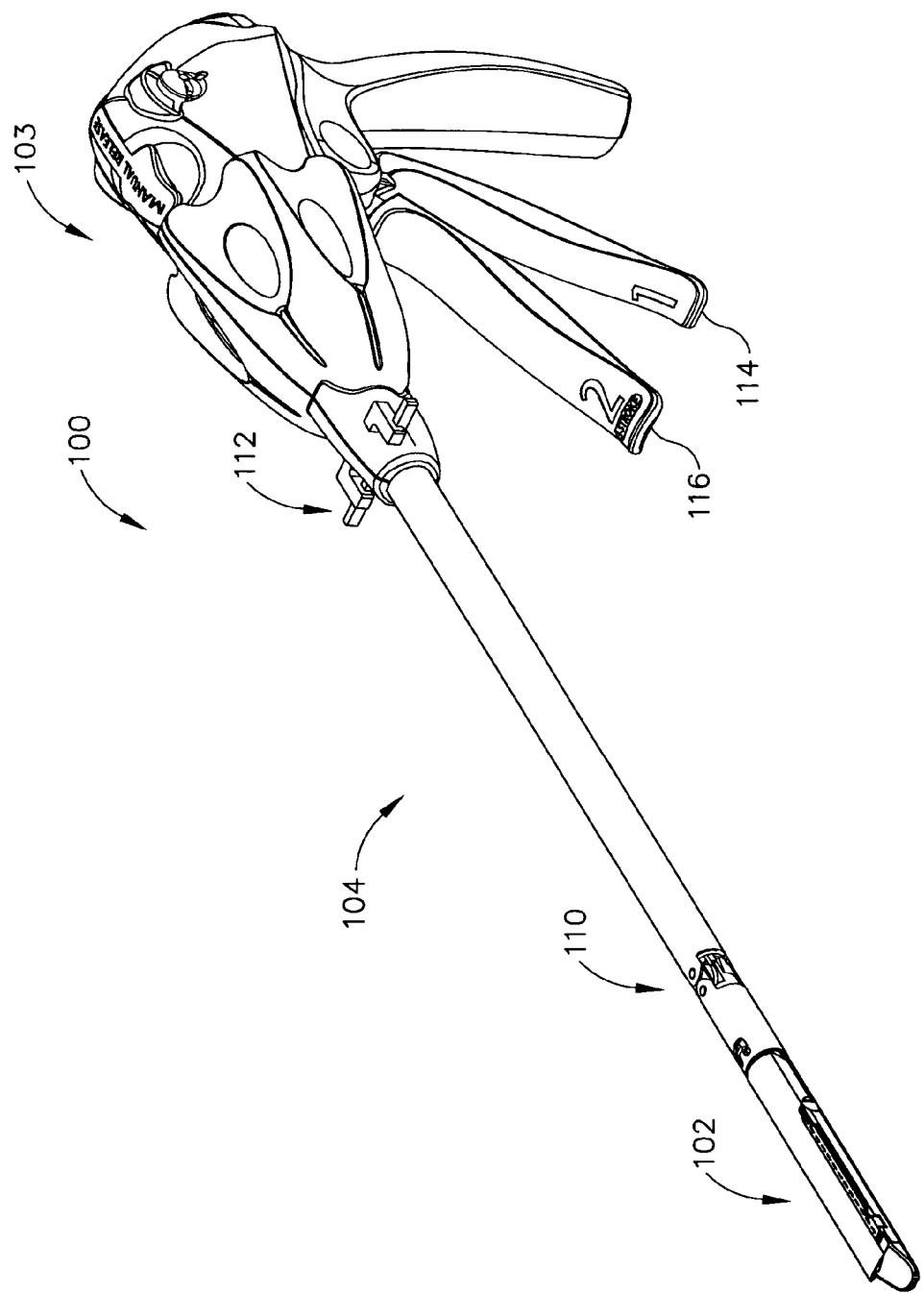
FIG. 3 depicts a three dimensional view of a surgical instrument according to various embodiments of the present invention.

FIGS. 3-5 show an exemplary surgical instrument 100 generally including a handle 103, a shaft 104 and an articulating end effector 102 pivotally connected to the shaft 104 at articulation pivot 110. An articulation control 112 is provided to effect rotation of the end effector 102 about articulation pivot 110. The end effector 102 is shown configured to act as an endocutter for clamping, severing and stapling tissue, however, it will be appreciated that various embodiments of the present invention may include end effectors (not shown) configured to act as other surgical devices including, for example, graspers, cutters, staplers, clip appliers, access devices, drug/gene therapy delivery devices, ultrasound, RF, or laser energy devices, etc.

The handle 103 of the instrument 100 may include closure trigger 114 and firing trigger 116 for actuating the end effector 102. It will be appreciated that instruments having end effectors directed to different surgical tasks may have different numbers or types of triggers or other suitable controls for operating an end effector. The end effector 102 is shown separated from a handle 103 by the preferably elongate shaft 104. A clinician may articulate the end effector 102 relative to the shaft 104 by utilizing the articulation control 112.

It should be appreciated that spatial terms such as vertical, horizontal, right, left etc., are given herein with reference to the figures assuming that the longitudinal axis of the surgical instrument 100 is co-axial to the central axis of the shaft 104, with the triggers 114, 116 extending downwardly at an acute angle from the bottom of the handle 103. In actual practice, however, the surgical instrument 100 may be oriented at various angles and as such these spatial terms are used relative to the surgical instrument 100 itself. Further, proximal is used to denote a perspective of a clinician who is behind the handle 103 who places the end effector 102 distal, or away from him or herself.

As used herein, the term "fluidically coupled" means that the elements are coupled together with an appropriate line or other means to permit the passage of pressurized fluid medium, air, etc. therebetween. As used herein, the term "line" as used in "supply line," "hydraulic line" or "return line" refers to an appropriate fluid passage formed from conduit, pipe, tubing, etc. for transporting pressurized hydraulic fluid from one component to another.

As used herein, the term, "hydraulic fluid" refers to any fluid suitable for use in a hydraulic system. Non-limiting examples of hydraulic fluids include oil, air, etc. In one non-limiting embodiment, hydraulic fluids may be biocompatible fluids including, for example, glycerin oil, saline, etc.

As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

Figure 6:
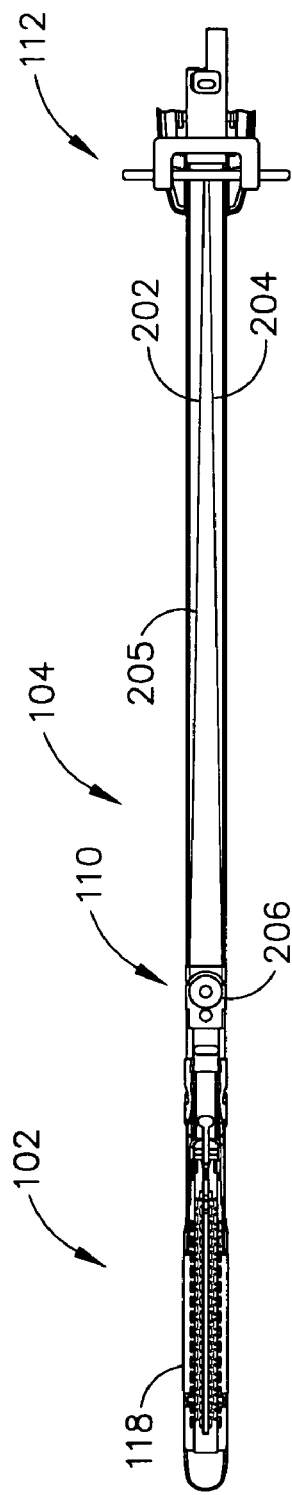
FIG. 6 depicts a top down cross-sectional view of an end effector and elongate, shaft of a surgical instrument according to one embodiment of the present invention.
Figure 7:
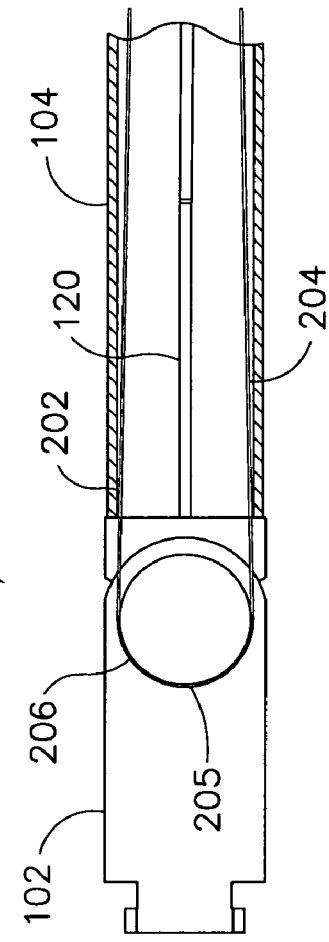
FIG. 7 depicts a top down cross-section view of an articulation pivot of the surgical instrument of FIG. 6 in a neutral position.

Various embodiments of the present invention are directed to instruments having an articulation pivot driven by bending cables or bands. FIG. 6 shows a cross-sectional top down view of an exemplary elongate shaft 104 and end effector 102 including a bending band driven articulation pivot 110. In the non-limiting embodiment of FIG. 6, band 205 is mechanically coupled to boss 206 located at the articulation pivot 110. The band 205 may include band portions 202 and 204 extending proximally from the boss 206 along the elongate shaft 104 and through the articulation control 112. The band 205 and band portions 202, 204 are preferably of a fixed length FIG. 7 shows a cross-sectional view of the articulation pivot 110 shown in FIG. 6 including the boss 206 and band 205. The band 205 may be mechanically coupled to the boss 206 as shown using any suitable fastening method including, for example, glue, welding, etc. In various embodiments, each band portion 202, 204 may be provided as a separate band, with each separate band having one end mechanically coupled to the boss 206 and another end extending through the shaft 104 and articulation controller 112 (not shown in FIG. 7). The separate bands may be mechanically coupled to the boss 206 as described above.

Figure 8:
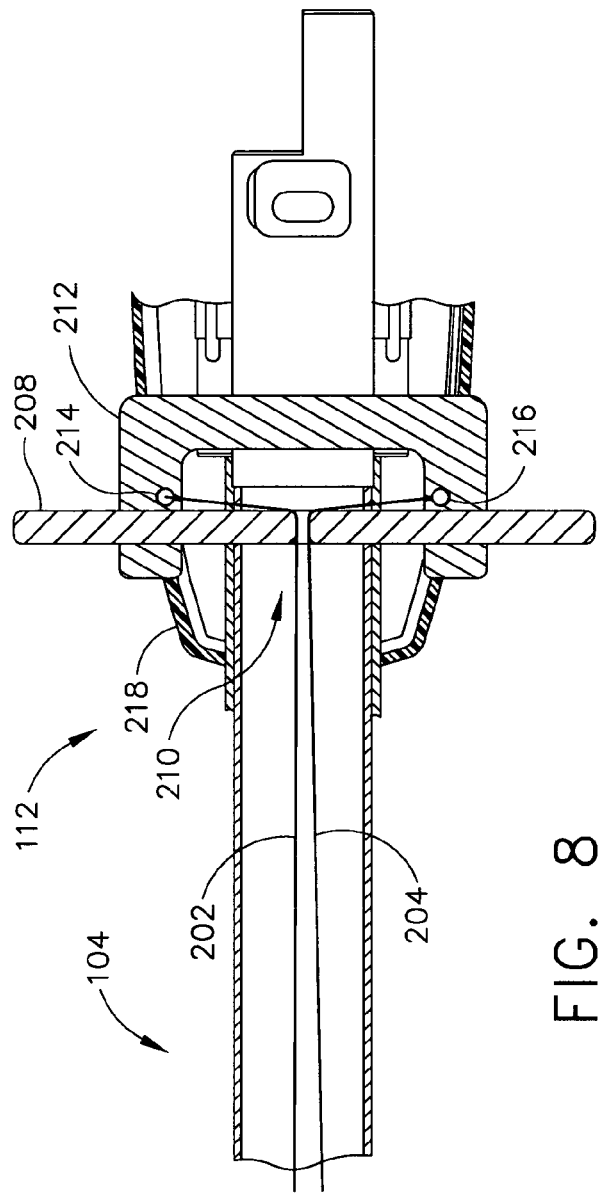
FIG. 8 depicts a top down cross-section view of an articulation control of the surgical instrument of FIG. 6 in a neutral position.
Figure 10:
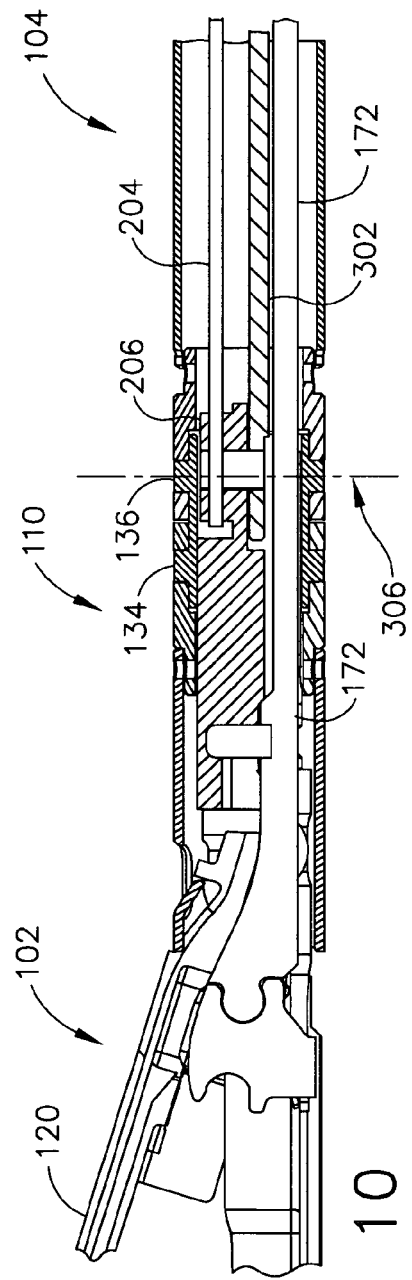
FIG. 10 depicts a side cross-section view of an articulation pivot of the surgical instrument of FIG. 6.

Band portions 202, 204 may extend from the boss 206, through the articulation pivot 110 and along the shaft 104 to the articulation control 112, shown in FIG. 8. The articulation control 112 may include an articulation slide 208, a frame 212 and an enclosure 218. Band portions 202, 204 may pass through the articulation slide 208 by way of slot 210 or other aperture, although it will be appreciated that the band portions 202, 204 may be coupled to the slide 208 by any suitable means. The articulation slide 208 may be one piece, as shown in FIG. 8, or may in one non-limiting embodiment, include two pieces with an interface between the two pieces defining the slot 210. In one non-limiting embodiment, the articulation slide 208 may include multiple slots, for example, with each slot corresponding to one of band portions 202, 204. Enclosure 218 may cover the various components of the control 112 to prevent debris from entering.

In various embodiments, band portions 202, 204 may be anchored to the frame 212 at connection points 214, 216 proximally located from the slot 210. The non-limiting embodiment of FIG. 8 shows that the band portions 202, 204 are pre-bent from connection points 214, 216 to the slot 210, located near the longitudinal axis of the shaft 104. It will be appreciated that band portions 202, 204 may be anchored anywhere in the instrument 10 located proximally from the slot 210, including the handle 103.

Figure 9A:
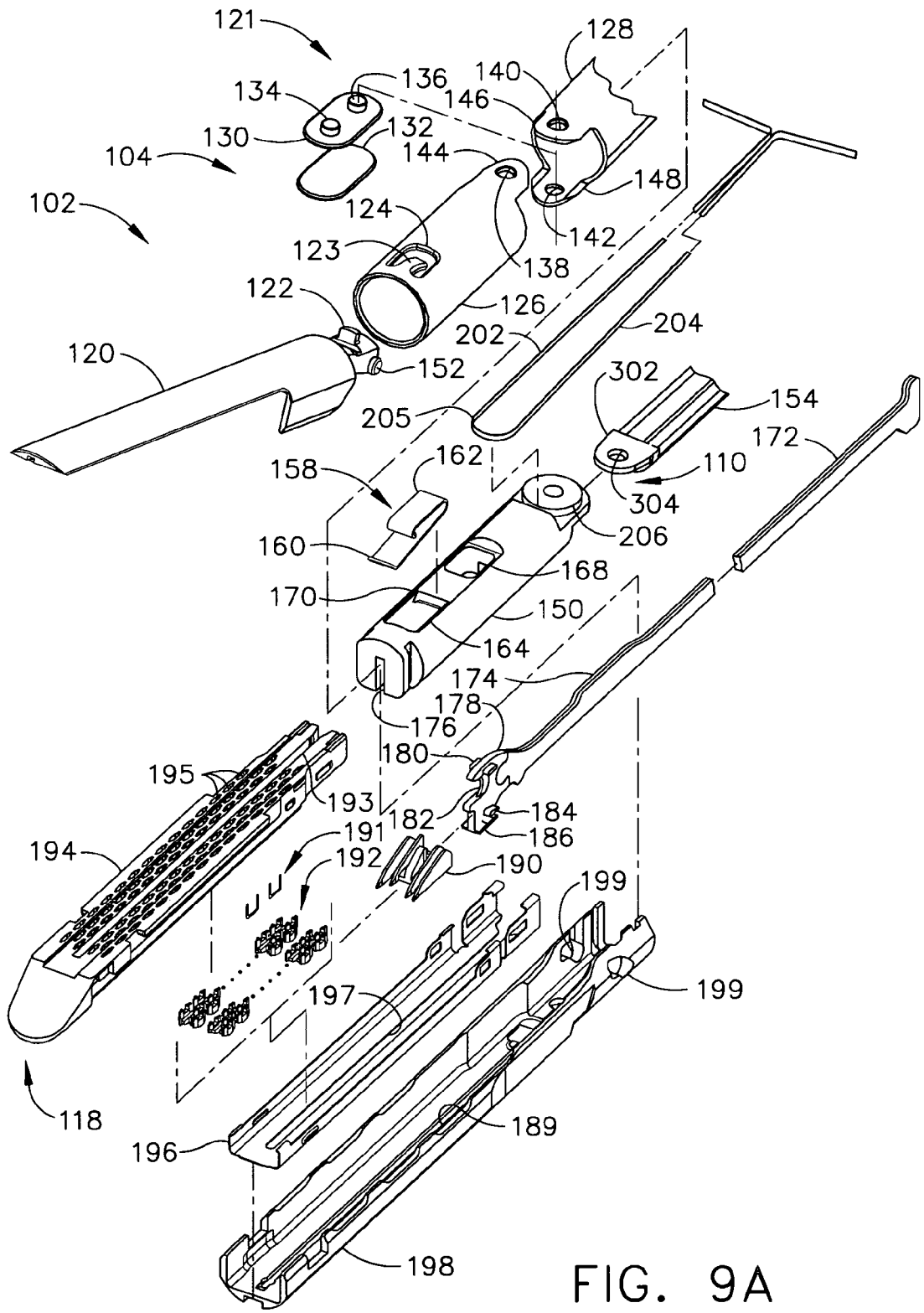
FIG. 9A depicts an exploded view of an end effector and elongate shaft of a surgical instrument having an articulation pivot like that of the instrument of FIG. 6.

FIGS. 9A-11 show views of the end effector 102 and elongate shaft 104 of the instrument 100 including the articulation pivot 110 shown in FIG. 7. The end effector 102 shown in FIGS. 9A-11 is configured to act as an endocutter. It will be appreciated that in various embodiments, the end effector 102 may be configured to perform other surgical tasks, requiring the removal, modification, or addition of components from what is shown in the figures. Also, it will be appreciated that the end effectors 102 shown in FIGS. 3-6, 11 may be customized for specific surgical applications. For example, FIGS. 3-6 and 10-12 show a 45 mm endocutter end effector while FIG. 9A shows a 60 mm endocutter end effector.

FIG. 9A shows an exploded view of the end effector 102 and elongate shaft 104 including various internal components. An end effector frame 150 and shaft frame 154 are configured to be joined at articulation pivot 110. Boss 206 may be integral to the end effector frame 150 with band 205 interfacing the boss 206 as shown. The shaft frame 154 may include a distally directed tang 302 defining an aperture 304. The aperture 304 may be positioned to interface an articulation pin (not shown) included in end effector frame 150 allowing the end effector frame 150 to pivot relative to the shaft frame 154, and accordingly, the end effector 102 to pivot relative to the shaft 104. When assembled, the various components may pivot about articulation pivot 110 at an articulation axis 306 shown in FIGS. 10 and 11.

FIG. 9A also shows an anvil 120. In this non-limiting embodiment, the anvil 120 is coupled to the elongate channel 198. For example, apertures 199 of the elongate channel 198 may receive pins 152 of the anvil 120, allowing the anvil 120 to pivot from an open position to a closed position relative to the elongate channel 198 and staple cartridge 118. A spring clip 158 is mounted in the end effector frame 150 as a lockout for firing bar 172. Distal and proximal square apertures 164, 168 formed on top of the end effector frame 150 may define a clip bar 170 therebetween that receives a top arm 162 of a clip spring 158 whose lower, distally extended arm 160 asserts a downward force on a raised portion 174 of the firing bar 172 discussed below. It will be appreciated that various embodiments may include other types of lockouts or no lockouts at all.

Figure 9B:
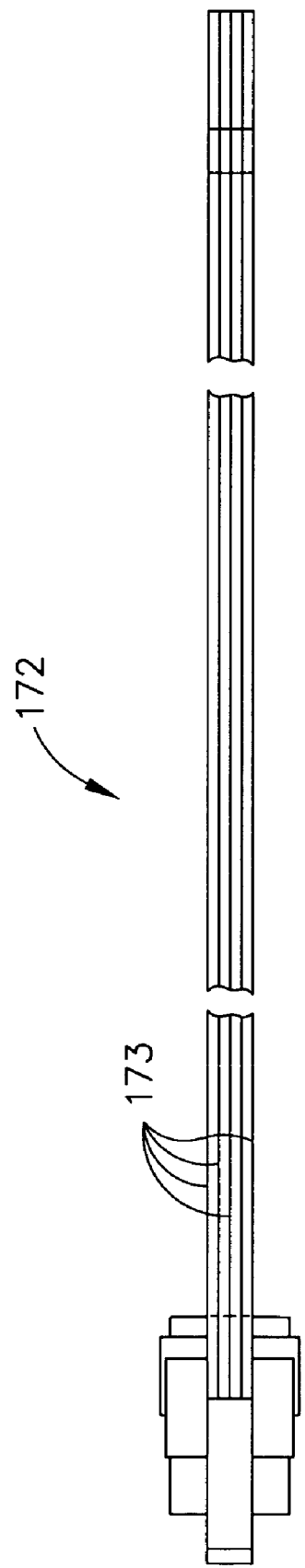
FIG. 9B depicts a top down view of the firing bar of the instrument of FIG. 9.
Figure 11:
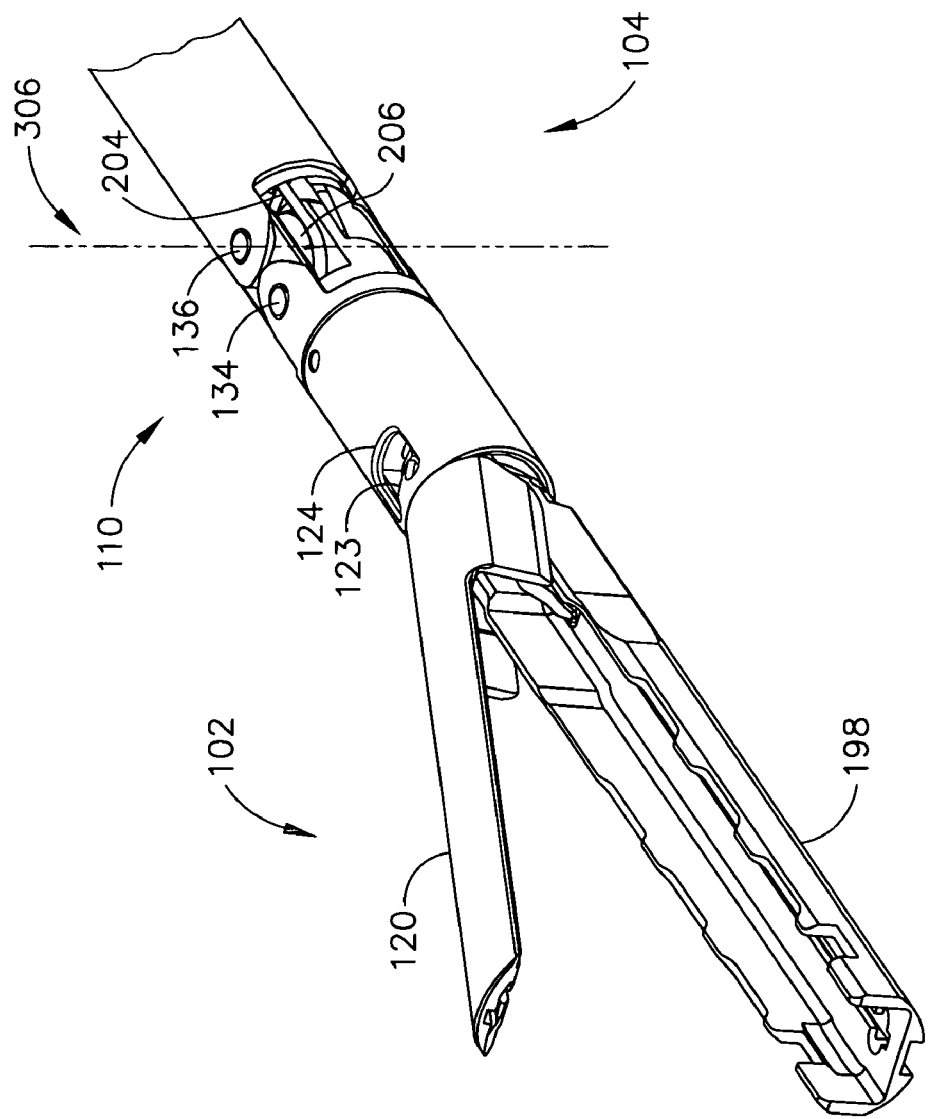
FIG. 11 depicts a three dimensional view of an end effector and articulation pivot of the surgical instrument of FIG. 10.

In addition, FIG. 9A shows the firing bar 172, configured to longitudinally translate through the shaft frame 154, through the flexible closure and pivoting frame articulation joint 110, and through a firing slot 176 in the distal frame ground 150 into the end effector 102. The firing bar 172 may be constructed from one solid section, or in various embodiments, may include a laminate material comprising, for example, a stack of steel plates 173 as shown in FIG. 9B. It will be appreciated that a firing bar 172 made from a laminate material may lower the force required to articulate the end effector 102. A distally projecting end of the firing bar 172 is attached to an E-beam 178 that assists in spacing the anvil 120 from the staple cartridge 118 when the anvil 120 is in a closed position. Sharpened cutting edge 182 of the E-beam 178 may also be used to sever tissue.

In operation, the E-beam 178 actuates the staple cartridge 118. The staple cartridge 118 includes a molded cartridge body 194 that holds a plurality of staples 191 resting upon staple drivers 192 within respective upwardly open staple apertures 195. A wedge sled 190 is driven distally by the E-beam 178, sliding upon a cartridge tray 196 that holds together the various components of the replaceable staple cartridge 118. The wedge sled 190 upwardly cams the staple drivers 192 to force out the staples 191 into deforming contact with the anvil 120 while a cutting surface 182 of the E-beam 178 severs clamped tissue.

In the figures, the firing bar 172 is shown positioned within the shaft 104 such that it passes through the cartridge 194 when the instrument 100 is fired. In one non-limiting embodiment, the firing bar 172 is instead positioned within the shaft 104 such that all or a portion of the body of the firing bar element 172 is supported by a slot (not shown) in the anvil 120 during firing. Because the anvil 120 may be stronger than the cartridge 118, support from the slot may preventing the firing bar 172 from buckling, even when high loads are applied to the distal end of the firing bar 178. This may be useful in embodiments where the firing bar element 172 includes laminate plates 173.

It should be appreciated that upper pins 180 of the E-beam 178 engage the anvil 120 during firing while middle pins 184 and a bottom foot 186 engage various portions of the cartridge body 194, cartridge tray 196 and elongate channel 198. In use, slot 193 of the cartridge body 194 aligns with slot 197 of the cartridge tray 196 and with slot 189 of the elongate channel 198. The leading edge of E-beam 178 slides through the aligned slots 193, 197, and 189. As indicated in FIG. 9A, the bottom foot 186 engages a groove running along the bottom surface of channel 198 along the length of slot 189. The middle pins 184 engage the top surfaces of cartridge tray 196 along the length of longitudinal slot 197. The foot 186 is braced against the bottom of channel 198 and the upper pins 180 are braced in a groove in the bottom surface of the anvil 120 to prevent the anvil 120 and channel 198 from being forced apart from resistance of tissue as the end effector is advanced by the clinician or surgeon during use. Thereafter, the firing bar 172 is retracted proximally, retracting as well the E-beam 178, allowing the anvil 120 to be opened to release the two stapled and severed tissue portions (not shown).

FIGS. 9A-11 also show a double pivot closure sleeve assembly 121 according to various embodiments of the present invention. It will be appreciated that the invention is not limited to a double pivot closure sleeve design and may include any suitable closure sleeve, or no closure sleeve at all.

With particular reference to FIG. 9A, the double pivot closure sleeve assembly 121 includes a shaft closure tube section 128 having upper and lower distally projecting tangs 146, 148. An end effector closure tube section 126 includes a horseshoe aperture 124 and tab 123 for engaging the opening tab 122 on the anvil 120. The horseshoe aperture 124 and tab 123 engage tab 122 when the anvil 120 is opened. The closure tube section 126 is shown having upper 144 and lower (not visible) proximally projecting tangs. An upper double pivot link 130 includes upwardly projecting distal and proximal pivot pins 134, 136 that engage respectively an upper distal pin hole 138 in the upper proximally projecting tang 144 and an upper proximal pin hole 140 in the upper distally projecting tang 146. A lower double pivot link 132 includes downwardly projecting distal and proximal pivot pins (not shown in FIG. 9A, but see FIG. 10) that engage respectively a lower distal pin hole in the lower proximally projecting tang and a lower proximal pin hole 142 in the lower distally projecting tang 148.

In use, the closure sleeve assembly 121 is translated distally to close the anvil 120, for example, in response to the actuation of the closure trigger 114. The anvil 120 is closed by distally translating the closure tube section 126, and thus the sleeve assembly 121, causing it to strike a proximal surface on the anvil 120 located in FIG. 9A to the left of the tab 122. As shown more clearly in FIGS. 10 and 11, the anvil 120 is opened by proximally translating the tube section 126, and sleeve assembly 121, causing tab 123 and the horseshoe aperture 124 to contact and push against the tab 122 to lift the anvil 120. In the anvil-open position, the double pivot closure sleeve assembly 121 is moved to its proximal position.

In operation, the clinician may articulate the end effector 102 of the instrument 100 relative to the shaft 104 about pivot 110 by pushing the control 112 laterally. Referring to FIGS. 6 and 8, it will be appreciated that if the band portions 202, 204 are of a fixed length and were to remain taut during articulation, then transverse force provided by the articulation control may not cause bending because, for example, band portion 204 would prevent the end effector 102 from rotating as the band portion 202 was bent. Accordingly, in the non limiting embodiment shown in FIG. 8, the band 205 is constructed such that band portions 202 and 204 are slightly longer than they need to be to articulate the end effector 102. The band portions 202, 204 are then pre-bent toward the slot 210, which is in line with longitudinal axis of the shaft 104 when the end effector 102 is in a neutral position.

From the neutral position, the clinician may articulate the end effector 102 to the left relative to the shaft 104 by providing a lateral force to the left side of the control 112. In response to force, the articulation slide 208 may be pushed through the frame 212 as shown in FIGS. 12 and 13. As the slide 208 is pushed through the frame 212, the slot 210 as well as band portion 204 may be translated across the elongate shaft 104 in a transverse direction, for example, a direction substantially transverse, or perpendicular, to the longitudinal axis of the shaft 104. Accordingly, a force is applied to band portion 204, causing it to further bend from its initial pre-bent position toward the opposite side of the shaft 104. At the same time, band portion 202 is relaxed from its initial pre-bent position. The further bending of band portion 204 coupled with the straightening of band portion 202 causes a counterclockwise rotational force at boss 206, which in turn causes the boss 206 and end effector 102 to pivot to the left about the articulation pivot 110 to a desired angle relative to the axis of the shaft 104 as shown in FIG. 12. The relaxation of band portion 202 decreases the tension on that band portion, allowing the band portion 204 to articulate the end effector 102 without interference from the band portion 202. It will be appreciated that the clinician may also articulate the end effector 102 to the right relative to the shaft 104 by providing a lateral force to the right side of the control 112. This bends cable portion 202, causing a clockwise rotational force at boss 206 which, in turn, causes the boss 206 and end effector to pivot to the right about articulation pivot 110.

Figure 15:
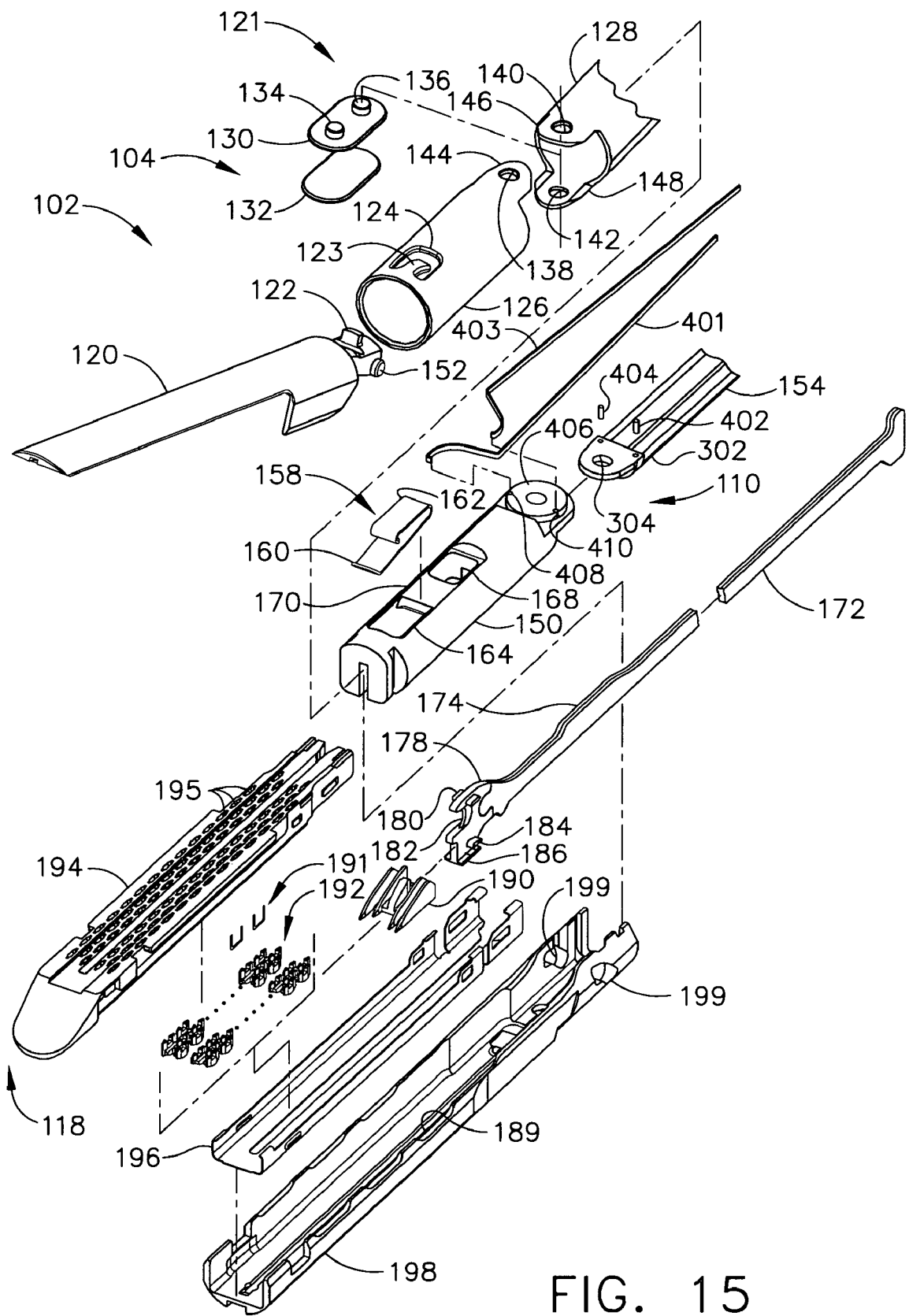
FIG. 15 depicts an exploded view of an end effector and elongate shaft of a surgical instrument having an articulation pivot like that of the instrument of FIG. 14.

FIGS. 14-18 illustrate an additional embodiment for articulating the end effector 102 with bending bands according to various embodiments. It will be appreciated that any kind of end effector 102 may be used with the embodiments shown in FIGS. 14-18. For example, FIGS. 14 and 16-18 show all or part of a 45 mm endocutter end effector while FIG. 15 shows a 60 mm endocutter end effector. FIG. 14 shows a cross-sectional view of the articulation pivot 110 including bands 401, 403 and boss 406. The bands 401, 403 may extend distally toward the articulation pivot 110 as shown. Band 401 may extend through the shaft 104 along its left side where it is routed around band member 402 and across to the right side of the shaft 104. There, the band 401 may be mechanically coupled to boss 406, for example, at connection point 408. Likewise, band 403 may extend through the shaft 104 along its right side where it is routed around band member 404 and across to the left side of the shaft. There, band 403 may be mechanically coupled to the boss 406 at connection point 410.

FIG. 16 shows a side cross-sectional view of the pivot 110. Bands 401 and 403 are shown offset from one another to prevent interference in movement according to one non-limiting embodiment. For example, band 401 is shown at a lower position than band 403. In another non-limiting embodiment, the vertical positioning of bands 401 and 403 may be reversed. FIG. 15 shows an exploded view of the end effector 102 and shaft 104 including internal components. The end effector 102 shown in FIG. 15 is configured to act as an endocutter for clamping, stapling, and severing tissue, however, it will be appreciated that various embodiments may utilize end effectors (not shown) directed to other surgical tasks. Band members 402, 404 are shown attached to shaft frame tang 302. Also, boss 406 may include connection points 408, 410 as shown. When assembled, the various components may pivot about articulation pivot 110 at an articulation axis 306 shown in FIG. 16.

Figure 17:
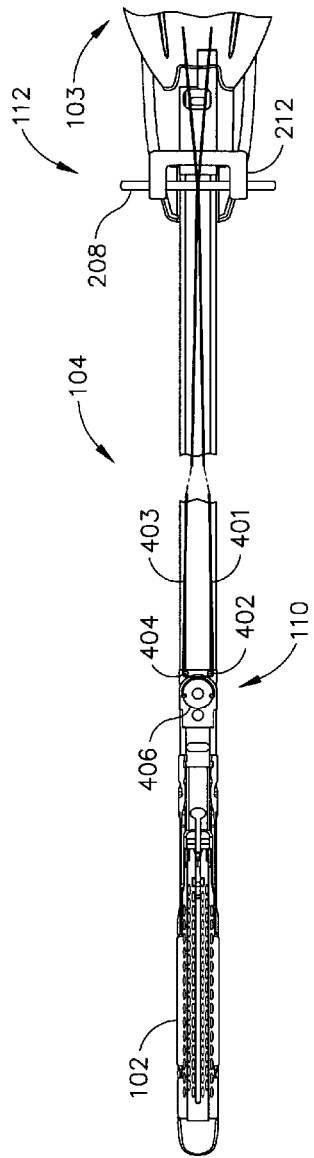
FIG. 17 depicts the end effector, articulation pivot, and articulation control of the surgical instrument of FIGS. 14-16 with the end effector in a neutral position.
Figure 18:
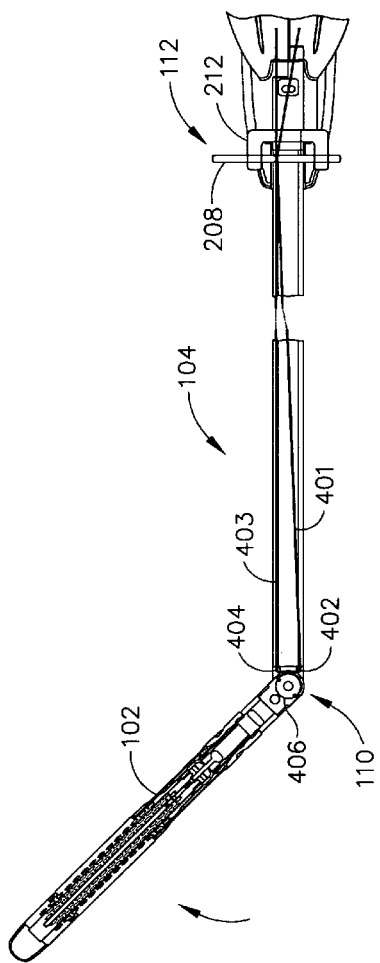
FIG. 18 depicts the end effector, articulation pivot, and articulation control of the surgical instrument of FIGS. 14-16 with the end effector articulated to the left.

In use, the embodiment of FIG. 14 may have an unarticulated position as shown in FIG. 17. The articulation control 112 and bands 401, 403 are shown in a centered position roughly at the longitudinal axis of the shaft 104. Accordingly, the end effector 102 is in a neutral or unarticulated position. In FIG. 18, the articulation control 112 is shown with the articulation slide 208 pushed through the articulation frame to the right side of the shaft 104. Accordingly, bands 401 and 403 are bent toward the right side of the shaft 104. It can be seen that the bending of band 401 to the right exerts a laterally directed force on the boss 406 that is offset from the boss's 406 pivot point. This offset force causes the boss 406 to rotate about articulation pivot 110, in turn causing the end effector 102 to pivot to the right as shown. It will be appreciated that pushing the articulation slide 208 to the left side of the shaft 104 may exert a laterally directed force on bands 401 and 403, bending both bands 401, 403 toward the left side of the shaft 104. The bending of band 403 then exerts a laterally directed force on boss 406, which as above, is offset from the boss's 406 pivot point. This, in turn, causes the boss 406 to rotate about the articulation pivot causing the end effector 102 to pivot to the left.

Figure 19:
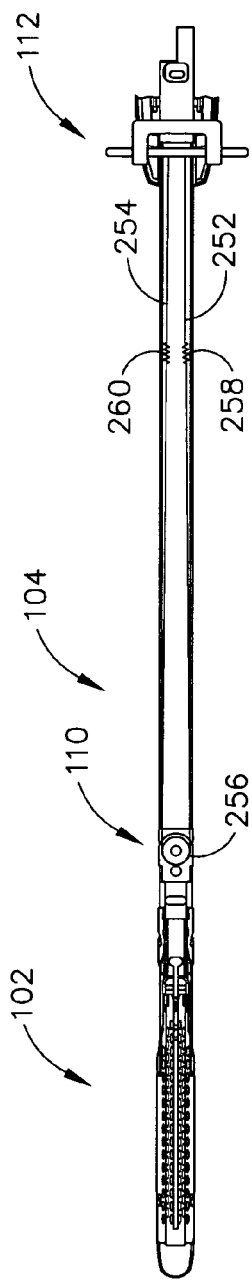
FIG. 19 depicts a top-down cross-sectional view of a surgical instrument according to one embodiment of the present invention.

FIGS. 19-24 show another embodiment for articulating the end effector 102 with bands 252, 254 oriented to interface with the articulation control 112 at points offset from the longitudinal axis of the shaft 104. Accordingly, the bands 252, 254 are substantially more parallel to each other within the shaft 104 than band portions 202, 204 or bands 401, 403 shown in FIGS. 6 and 17 respectively. FIG. 19 shows a top-down cross section of an exemplary shaft 104, end effector 102 and articulation control 112 according to the embodiment of FIGS. 19-24. The bands 252, 254 are shown extending from a boss 256 through the shaft 104 to the articulation control 112. Spring assemblies 258 and 260 are included along the length of bands 252, 254 allowing the bands to lengthen. It will be appreciated that bands 252, 254 may be separate bands, similar to, for example, bands 401, 403 shown in FIGS. 14-18, or may be one band with two portions similar to band 205 and band portions 202, 204 shown in FIGS. 6-13. Similarly, it will be appreciated that the bands 252, 254 may be routed from the boss 256 around band members (not shown) similar to band members 402, 404 shown in FIGS. 14-18.

Figure 20:
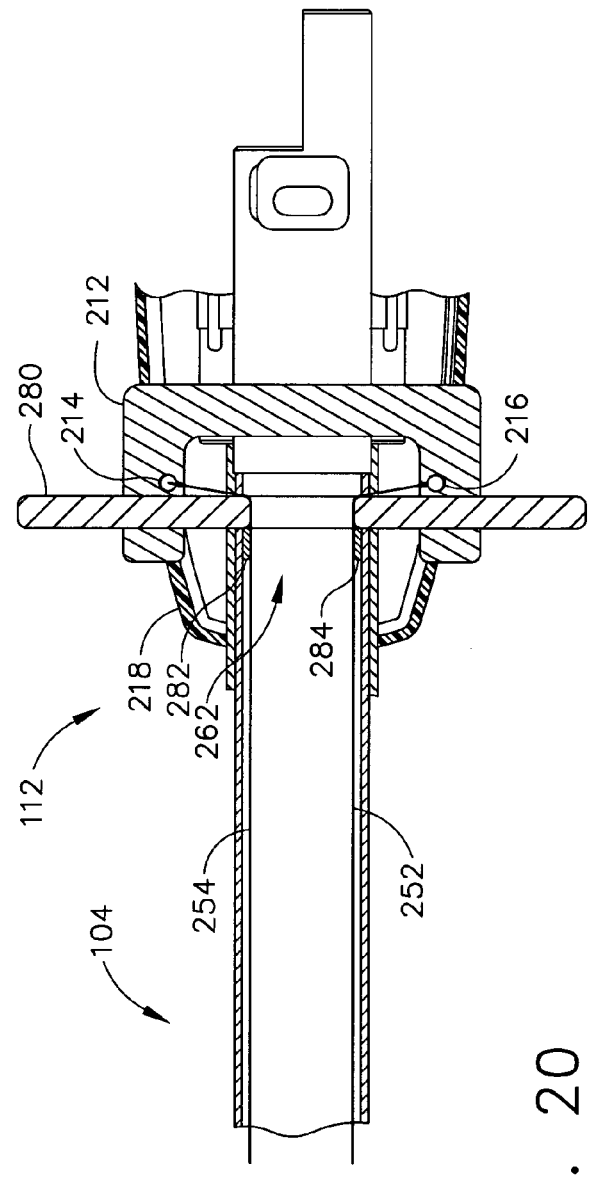
FIG. 20 depicts a top-down cross-sectional view of an articulation control of the surgical instrument of FIG. 19 in a neutral position.

FIG. 20 shows a top-down cross section of an exemplary interface between the shaft 104 and articulation control 112 according to the embodiment of FIGS. 19-24. Bands 252, 254 may extend through the shaft 104 and interface the articulation control 112 at slide opening 262 of articulation slide 280 before being anchored to the articulation control 112 at connection points 214, 216. The bands 252, 254 may be pre-bent between the slide opening 262 and connection points 214 and 216. It will be appreciated, however, that because the bands 252, 254 interface the articulation control 112 at points offset from the center of the shaft 104, they are not pre-bent to the same degree as the band portions 202 or 204 shown in FIG. 8.

Figure 21:
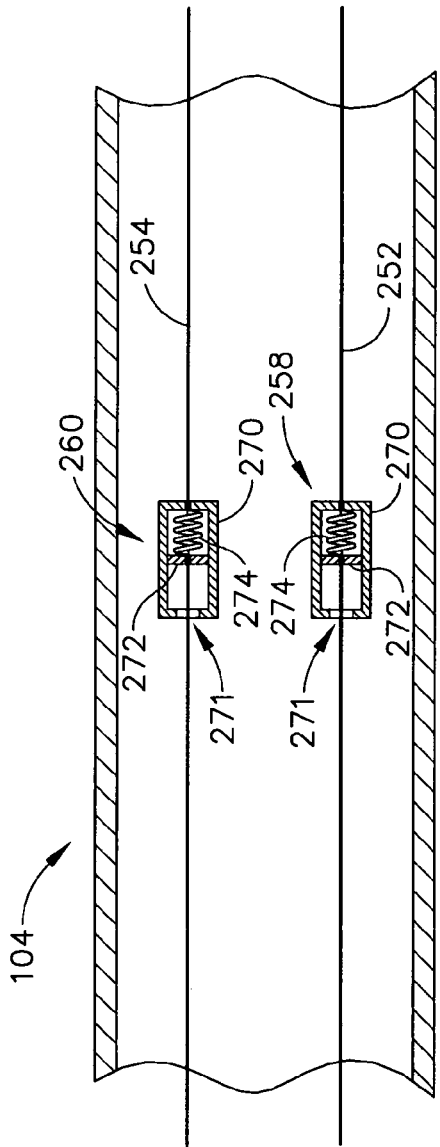
FIG. 21 depicts a top-down cross-sectional view of the shaft, cables, and spring assemblies of the surgical instrument of FIG. 19 in a neutral position.

FIG. 21 shows a close-up cross sectional view of spring assemblies 258, 260. The spring assemblies 258 and 260 are configured to allow the bands 252, 254 to lengthen under low tension, but arrest the expansion of the bands 252, 254 under high tension. Referring to the spring assemblies 258, 260, a piston 272 rides within a shell 270. A spring 274 is coupled to the piston 272 as well as the shell 270. When the cable 252 or 254 is under a slight tension, then the spring 274 will lengthen slightly, allowing the piston 272 to move toward the opening 271 of the shell 270. When the cable 252 or 254 is under a greater tension, then the piston 272 will be moved into contact with the shell 270 near opening 271, preventing the spring assembly 258 or 260 from lengthening any further.

Figure 22:
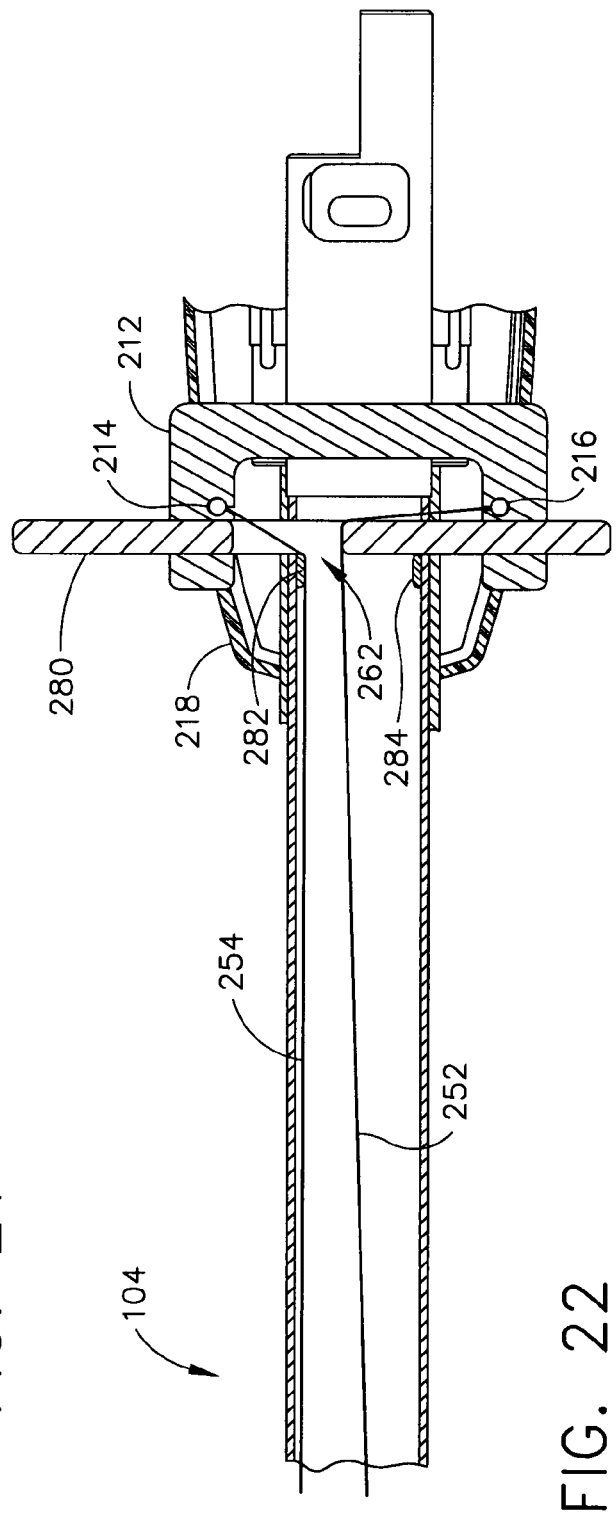
FIG. 22 depicts a top-down cross-sectional view of an articulation control of the surgical instrument of FIG. 19 articulated to the left.
Figure 23:
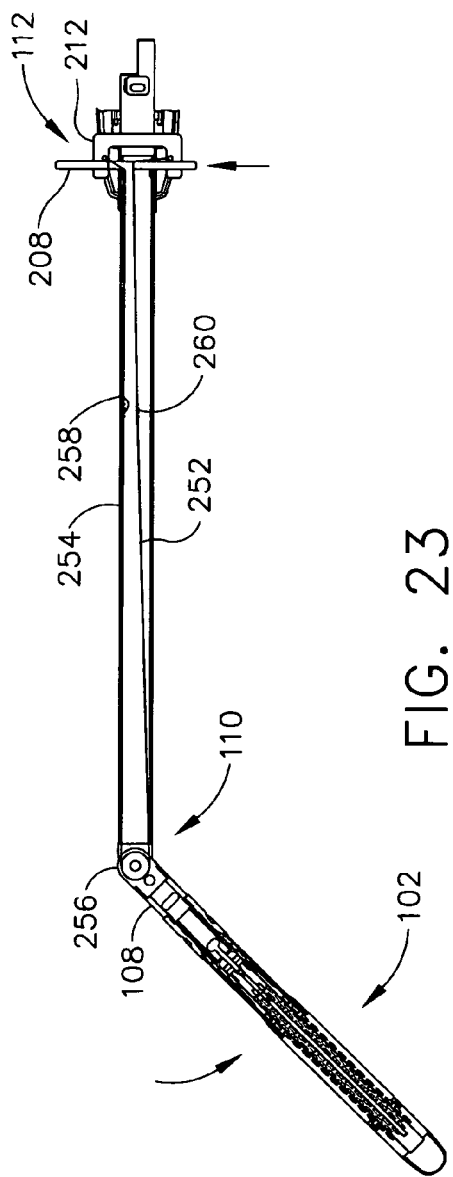
FIG. 23 depicts a top-down cross-sectional view of the surgical instrument of FIG. 19 articulated to the left.
Figure 24:
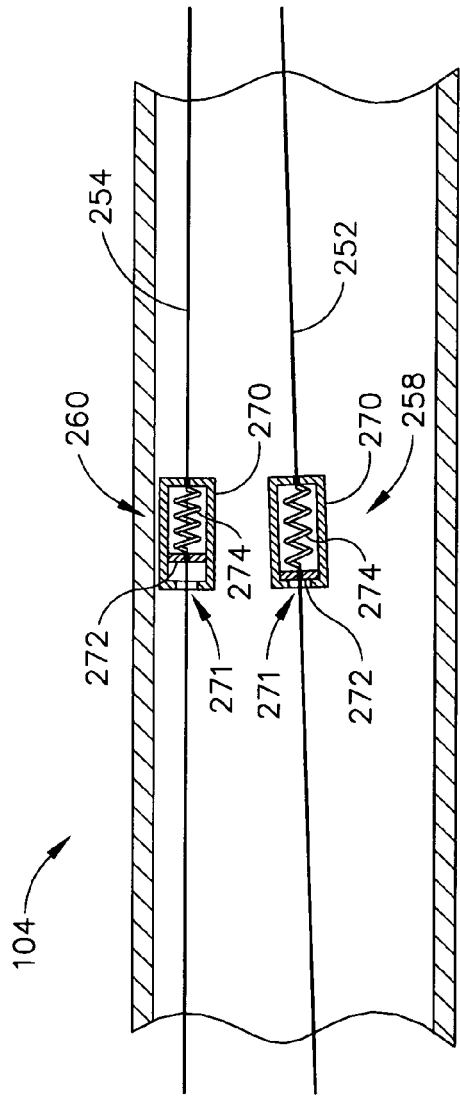
FIG. 24 depicts a top-down cross-sectional view of the shaft, cables, and spring assemblies of the surgical instrument of FIG. 19 articulated to the left.

FIG. 22 shows the articulation control 112 of FIG. 20 with the articulation slide 280 pushed from left to right across the longitudinal axis of the shaft 104. As a result, band 252 is bent toward the right side of the shaft 104, while band 254 is maintained in its original position by stop 282. Referring to FIG. 24, as the band 252 is initially bent by articulation control 112, the spring 274 of spring assembly 258 will lengthen until the piston 272 contacts the shell 270 and the spring assembly 258 can lengthen no more. At that point, continued bending of the cable 252 causes a counter-clockwise rotational force at the boss 256. As the boss 256 begins to rotate in response to the rotational force, it exerts a tension on the unbent band 254. Accordingly, the spring 274 of the spring assembly 260 may lengthen, lengthening band 254 and allowing the boss 256 to rotate in a counter-clockwise direction. The rotation of the boss 256 causes the end effector 102 to pivot to the leftward rotational direction, as shown in FIG. 23. It will be appreciated that the tension in band 254 is low enough that the spring assembly 260 will not reach its maximum expansion during the desired range of motion of the end effector 102.

Sliding the articulation slide 280 across the shaft 104 from right to left, the opposite of what is shown in FIGS. 22-24, causes band 254 to bend and effect a clockwise rotation of the boss 256 and rightward articulation of the end effector 102 with the roles of bands 252 and 254 reversed from the description above. Also, it will be appreciated that in various applications, it may only be necessary for the end effector 102 to pivot in one rotational direction relative to the shaft. Accordingly, the embodiment of FIGS. 19-24 may be implemented with only one spring assembly positioned on the band opposite the desired direction of articulation. The spring assembly, in that case, may be any kind of spring including, for example, an elastic portion of the appropriate band.

Figure 25:
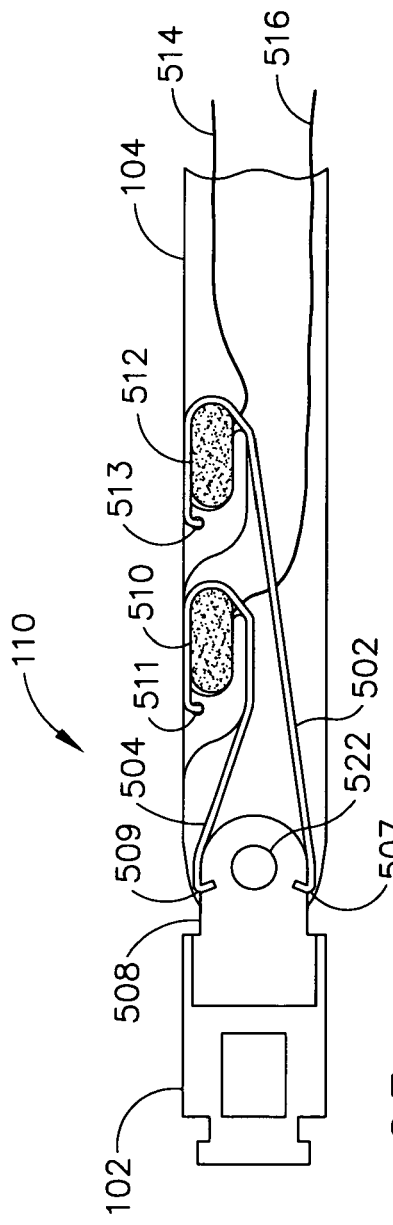
FIG. 25 depicts a top down cross-section view of an articulation pivot of a surgical instrument according to another embodiment of the present invention.
Figure 26:
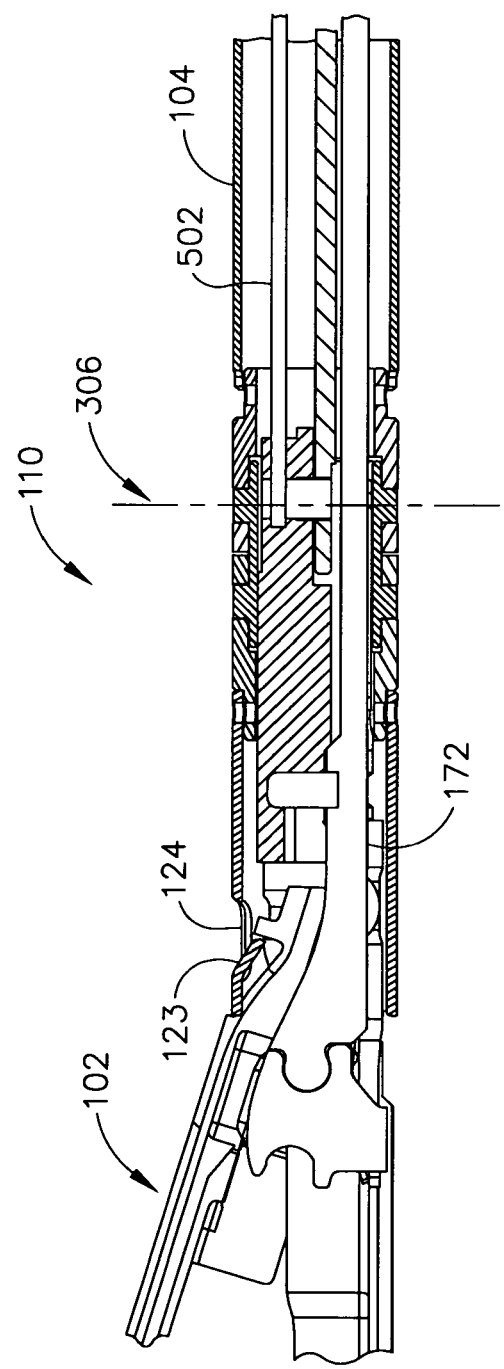
FIG. 26 depicts a side cross-section view of the articulation pivot of the surgical instrument of FIG. 25.
Figure 27:
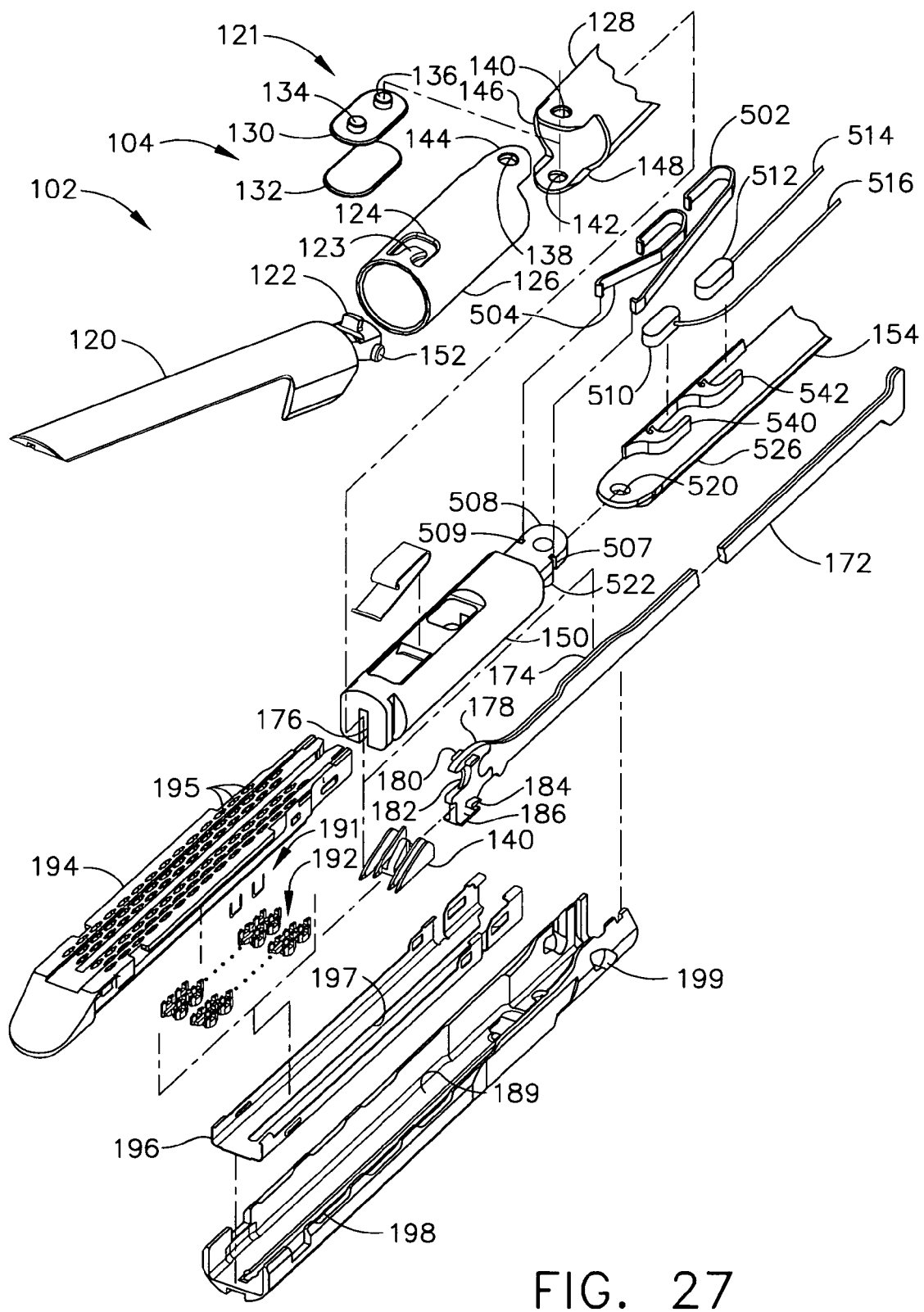
FIG. 27 depicts an exploded view of an end effector and elongate shaft of a surgical instrument having an articulation pivot like that of the instrument of FIGS. 25 and 26.

FIGS. 25-30 show an embodiment for hydraulically articulating the end effector 102 with bending cables or bands according to various embodiments. It will be appreciated that any kind of end effector 102 may be used with the embodiments shown in FIGS. 25-30. For example, FIGS. 25-26 and 29-30 show all or part of a 45 mm endocutter end effector while FIG. 27 shows a 60 mm endocutter end effector. Referring to FIG. 25, a member 508 is shown mechanically coupled to the end effector 102. The member 508 may be pivotally connected to shaft 104 at pin 522 in a manner allowing the end effector 102 and member 508 to pivot about the pin 522. The pin 522 may, in various embodiments, be located at the articulation axis 306 (shown in FIG. 26).

Bands 502, 504 may be coupled to the member 508, for example, at connection points 507 and 509 respectively. It will be appreciated that in various non-limiting embodiments, bands 502, 504 may be replaced with one band (not shown) that extends around member 508, for example, similar to the embodiment shown in FIG. 7 above. Referring back to FIG. 25, bands 502 and 504 may extend from the member 508 to connection points 513 and 511 respectively on the right side of the shaft 104. Each of the bands 502, 504, are also be positioned to be in effective contact with a respective hydraulic bladder 510, 512 as shown.

The bladders 510, 512 may expand proximally when supplied with pressurized hydraulic fluid, for example, through hydraulic lines 514 and 516. When expanded, bladders 510, 512 exert a proximal bending force on bands 502, 504. For example, when expanded, bladder 510 exerts a bending force on band 504, which in turn exerts a force offset to the member 508's pivot point, rotating the end effector 102 about the articulation axis 306 (shown in FIG. 26). In the embodiment shown in FIGS. 25-27 and 29-30, the bladders 510, 512 are both positioned on the right side of the shaft 104. It will be appreciated, however, that in other non-limiting embodiments, the bladders may be placed on the left side of the shaft 104, or each bladder 510, 512 may be placed on a different side of the shaft 104. Expansion of the bladders 510, 512 upon pressurization may be in any of several directions provided the expansion exerts a force against the band 502 or 504, with which the bladder is in effective contact, to effect the rotational force on the member 508 and end effector 102.

FIGS. 26-27 show additional views of the end effector 102 and shaft 104 according to the embodiment of FIG. 25. FIG. 27 shows an exploded view of components present in the end effector 102 and shaft 104. End effector frame 150 is shown mechanically coupled to member 508. In various non-limiting embodiments, the member 508 may be an integral portion of the end effector frame 150. A shaft frame 526 is shown to include pin aperture 520. Pin 522 may engage pin aperture 518, defined by member 508, thereby fastening member 508 to the shaft frame 526 and allowing the member 508 and end effector 102 to rotate about pin 522. The shaft frame 526 is also shown to include hydraulic bladder pockets 540 and 542 for enclosing hydraulic bladders 510 and 512, respectively.

Figure 28:
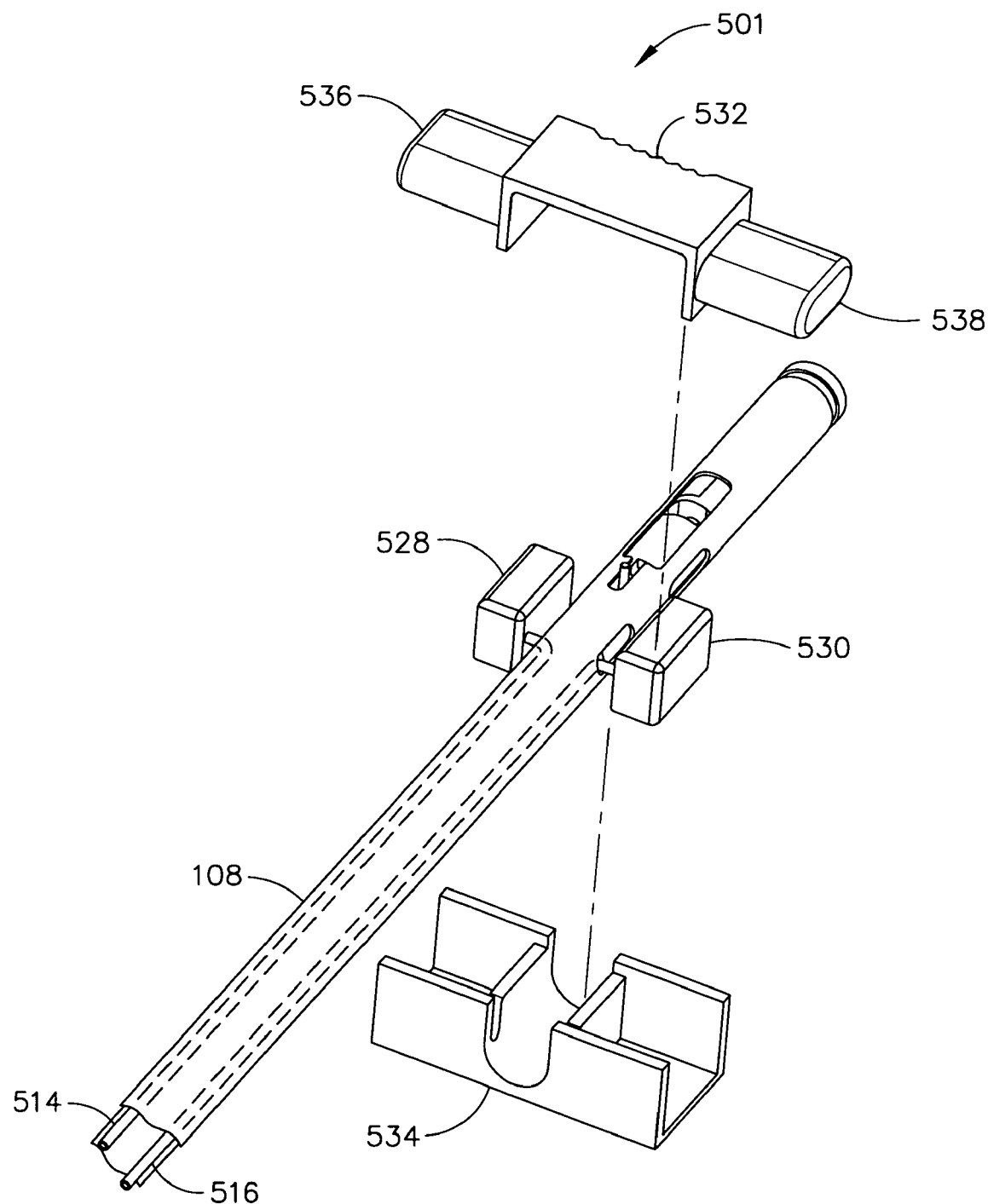
FIG. 28 depicts a hydraulically actuated articulation control of a surgical instrument useful to the embodiment of the present invention shown in FIGS. 25 and 26.

The hydraulic bladders 510 and 512 may be operated using the articulation control 501 shown in FIG. 28. Left and right actuation bladders 528, 530 included in articulation control 501, when actuated, provide pressurized hydraulic fluid to hydraulic lines 514, 516. The actuation bladders 528, 530 may be enclosed in a frame assembly including a top portion 532 and a bottom portion 534. Left and right buttons 536, 538 included in the frame assembly allow a clinician to compress one or the other of hydraulic bladders 528 or 530, thus actuating the hydraulic bladder 528 or 530 thereby forcing the hydraulic fluid from the bladder through its associated hydraulic line 514, 516 to the bladders 512 or 510 respectively, thus bringing about rotation of the end effector 102.

Figure 29:
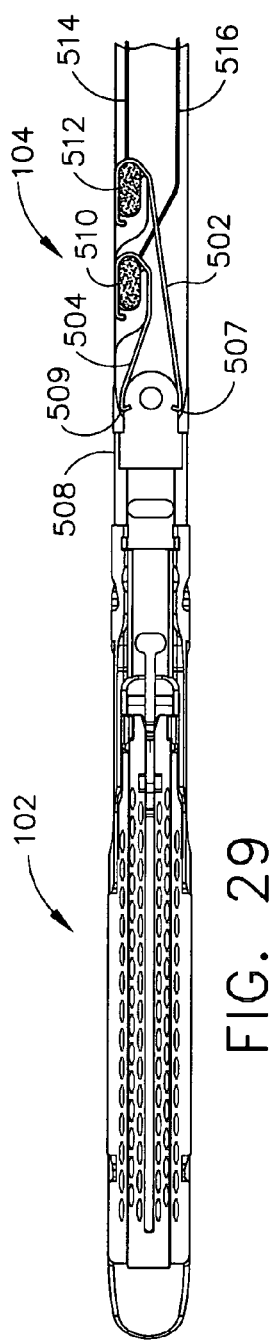
FIG. 29 depicts an end effector and articulation pivot of the surgical instrument of FIGS. 25-27 with the end effector in a neutral position.
Figure 30:
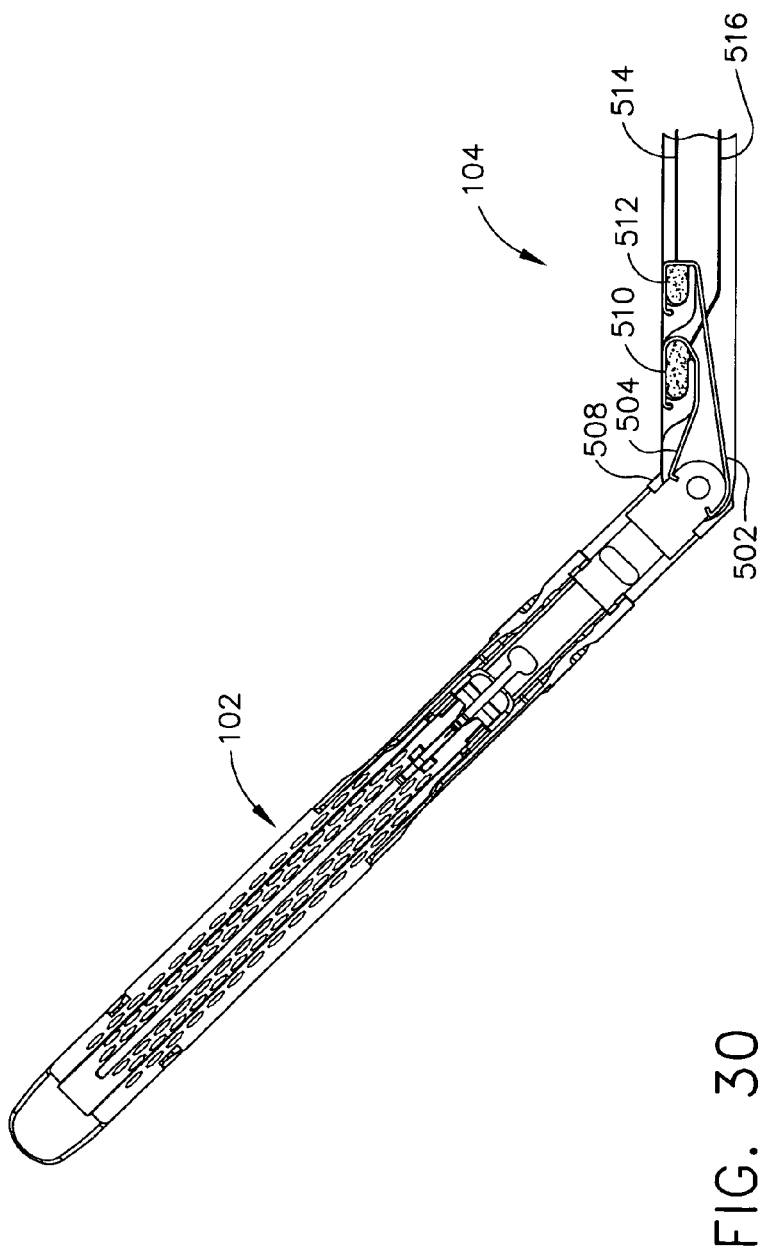
FIG. 30 depicts the end effector and articulation pivot of the surgical instrument of FIGS. 25-27 with the end effector articulated to the right.

FIGS. 29-30 show cross-sectional views of the embodiment of FIG. 25 in use. In FIG. 29, neither the bladder 510 nor the bladder 512 is expanded. Accordingly, the end effector 102 is shown in a neutral or unarticulated position. In contrast, FIG. 30 shows the bladder 510 in an inflated state. The bladder 510 inflates, for example, in response to pressurized hydraulic fluid provided through hydraulic line 516. In its inflated state, the bladder 510 is expanded to provide a bending force to band 504. The band 504 then exerts a force offset to the member's 508 pivot point to rotate the member 508 in a clockwise rotational direction, causing the end effector 102 to articulate to the right as shown.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although the embodiments described above have advantages for an endoscopically employed surgical severing and stapling instrument 100, a similar embodiments may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is believed that the present invention may find use in any procedure where access is limited to a small incision, including but not limited to laparoscopic procedures, as well as open procedures.

For yet another example, although an illustrative handle portion 103 described herein is operated mechanically in response to input from a clinician, it is consistent with aspects of the invention for some or all of the functions of a handle portion to be powered by other means (e.g., pneumatic, electromechanical, ultrasonic, hydraulic, etc.). Furthermore, controls of each of these functions may be manually presented on a handle portion or be remotely controlled (e.g., wireless remote, automated remote console, etc.).

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

We claim:

1. An articulating surgical instrument, the instrument comprising:
    a shaft having a longitudinal axis;
    an end effector operationally coupled to the shaft at an articulation pivot, wherein the end effector comprises a boss centered on the articulation pivot;
    a first band operationally connected to the end effector and extending through at least a portion of the shaft, wherein the first band is mechanically coupled to the end effector at a first point of the boss that is offset from the articulation pivot such that force translated through the first band is translated to the boss to effect rotation of the boss about the articulation pivot; and
    an articulation control, wherein the articulation control comprises an articulation slide that is movable substantially perpendicularly across the shaft for applying a force in a direction substantially perpendicular to the longitudinal axis, said articulation slide being operationally connected to the first band such that application of the force is translated through the first band to the end effector to effect rotation of the end effector relative to the shaft about the articulation pivot.

2. The instrument of claim 1, wherein the articulation control is structured for movement in a first direction for applying the force in a first direction to effect rotation of the end effector in a first rotational direction relative to the shaft.

3. The instrument of claim 2, wherein the articulation control is structured for movement in a second direction for applying the force in a second direction, opposite to the first direction, to effect rotation of the end effector in a second rotational direction relative to the shaft.

4. The instrument of claim 2, further comprising a second band operationally connected to and extending from the end effector through at least a portion of the shaft, the articulation control being operationally connected to the second band such that application of the force is translated through the second band to the end effector to effect rotation of the end effector in a second rotational direction relative to the shaft.

5. The instrument of claim 4, wherein the articulation slide is movable transversely across the shaft to first, second and neutral positions.

6. The instrument of claim 5, wherein the slide is movable transversely across the shaft to third and fourth positions.

7. The instrument of claim 5, wherein the first band and the second band are pre-bent toward the longitudinal axis when the articulation control is in the neutral position.

8. The instrument of claim 5, wherein the articulation slide defines a slot positioned at about the longitudinal axis when the articulation slide is in the neutral position and wherein the first band and the second band pass through the slot and the articulation slide is positioned offset from the longitudinal axis when the articulation slide is in one of the first and the second positions.

9. The instrument of claim 1, further comprising a first distal member, wherein the first band is routed from the end effector around the first distal member.

10. The instrument of claim 9, further comprising a second band operationally connected to and extending from the end effector through at least a portion of the shaft, and a second distal member, wherein the second band is routed from the end effector around the second distal member.

11. The instrument of claim 1, wherein the articulation slide contacts the first band during at least a portion of the range of motion of the articulation slide.

12. The instrument of claim 1, wherein the force is applied to the first band.

13. The instrument of claim 1, further comprising a second band operationally connected to and extending from the end effector through at least a portion of the shaft, wherein the articulation control is operationally connected to the second band, wherein the second band is mechanically coupled to the boss such that force applied to the second band is translated to the boss to effect rotation of the boss about the articulation pivot.

14. The instrument of claim 13, wherein the second band is mechanically coupled to the boss at a second point offset from the articulation pivot and spaced from the first point.

15. The instrument of claim 1, further comprising a handle mechanically connected to the shaft.

16. The instrument of claim 1, further comprising a second band operationally connected to and extending from the end effector through at least a portion of the shaft, and wherein the second band comprises a spring assembly allowing the second band to lengthen in response to tension.

17. The instrument of claim 16, wherein the first band further comprises a spring assembly allowing the first band to lengthen a fixed distance in response to tension.

18. The instrument of claim 16, wherein the first band and the second band are operationally connected to the articulation control at points offset from the longitudinal axis of the shaft.

19. The instrument of claim 16, wherein the second band is configured to receive a second force in a direction substantially transverse to the longitudinal axis, wherein the second force is translated through the second band to the end effector to effect rotation of the end effector relative to the shaft about the articulation pivot in a second direction.

20. An articulating surgical instrument, the instrument comprising:
- a shaft having a proximal end and a distal end, and a longitudinal axis;
- an end effector pivotally coupled to the shaft at an articulation pivot at the distal end of the shaft allowing the end effector to pivot relative to the shaft about an articulation axis, wherein the end effector comprises a boss centered on the articulation pivot;
- a first band extending through at least a portion of the shaft, the first band comprising a first end mechanically coupled to the end effector at a point offset from the articulation axis, wherein the first band is mechanically coupled to the end effector at a first point of the boss that is offset from the articulation pivot such that force translated through the first band is translated to the boss to effect rotation of the boss about the articulation pivot;
- an articulation control bar movable substantially perpendicularly across the shaft towards the first band for applying a force in a direction substantially perpendicular to the longitudinal axis.

21. The instrument of claim 20, further comprising a handle mechanically coupled to the shaft at the proximal end of the shaft.

22. The instrument of claim 20, further comprising a distal member positioned in the shaft, wherein the first band is routed to the end effector around the distal member.

23. The instrument of claim 20, further comprising a second band extending through at least a portion of the shaft, the second band comprising a first end mechanically coupled to the end effector at a second point offset from the articulation axis.

24. The instrument of claim 23, wherein the first band and the second band are pre-bent.

25. A method of operating a surgical instrument, wherein the surgical instrument comprises: a shaft; an end effector comprising a boss mechanically coupled to the shaft at an articulation pivot allowing the end effector to pivot relative to the shaft about an articulation axis; a first band extending through at least a portion of the shaft, the first band comprising a first end mechanically coupled to the boss of the end effector at a point offset from the articulation axis; and an articulation slide movable substantially perpendicularly to the shaft, the method for operating the instrument comprising:
- applying a force to the articulation slide in a direction that is substantially perpendicular to the shaft, wherein the force causes the articulation slide to contact the first band, causing the first band to bend, and wherein the bending of the first band causes the end effector to pivot relative to the shaft about the articulation pivot in a first direction.

26. The method of claim 25, wherein the surgical instrument further comprises a second band comprising a first end mechanically coupled to the end effector at a second point offset from the articulation axis, the method further comprising applying a second force to the instrument in a second direction that is substantially transverse to the shaft, wherein the second force causes the second band to bend, and wherein the bending of the second band causes the end effector to pivot relative to the shaft about the articulation pivot in a second direction.

* * * * *